(12) United States Patent
Frise et al.

(10) Patent No.: US 10,430,955 B2
(45) Date of Patent: Oct. 1, 2019

(54) HIGH CONTENT SCREENING WORKFLOWS FOR MICROSCOPE IMAGING

(71) Applicant: The Regents of the University of California, Oakland, CA (US)

(72) Inventors: Erwin Frise, Oakland, CA (US); Benjamin Booth, San Lorenzo, CA (US); Charles McParland, Berkeley, CA (US); Keith Beattie, Oakland, CA (US); Bill Fisher, Berkeley, CA (US); Ann S. Hammonds, Berkeley, CA (US); Susan E. Celniker, Lafayette, CA (US)

(73) Assignee: The Regents of the University of California, Oakland, CA (US)

( * ) Notice: Subject to any disclaimer, the term of this patent is extended or adjusted under 35 U.S.C. 154(b) by 201 days.

(21) Appl. No.: 15/692,552

(22) Filed: Aug. 31, 2017

(65) Prior Publication Data
US 2018/0061066 A1    Mar. 1, 2018

Related U.S. Application Data

(60) Provisional application No. 62/382,213, filed on Aug. 31, 2016.

(51) Int. Cl.
*G06K 9/00* (2006.01)
*G06T 7/33* (2017.01)
(Continued)

(52) U.S. Cl.
CPC ........... *G06T 7/337* (2017.01); *C12Q 1/6869* (2013.01); *G02B 21/365* (2013.01); *G06T 7/11* (2017.01); *G06T 7/168* (2017.01); *G06T 7/33* (2017.01); *H04N 5/23229* (2013.01); *H04N 5/23293* (2013.01); *G06T 2207/10016* (2013.01); *G06T 2207/10056* (2013.01); *G06T 2207/10148* (2013.01); *G06T 2207/10152* (2013.01); *G06T 2207/20056* (2013.01);
(Continued)

(58) Field of Classification Search
None
See application file for complete search history.

(56) References Cited

U.S. PATENT DOCUMENTS 5,428,690 A * 6/1995 Bacus .............. G01N 35/00029
356/39
5,889,881 A * 3/1999 MacAulay ......... G01N 15/1475
382/133
(Continued)

OTHER PUBLICATIONS

Ballard, Generalizing the hough transform to detect arbitrary shapes, Pattern Recognition, 1981, 13(2):111-122.
(Continued)

*Primary Examiner* — Shervin K Nakhjavan
(74) *Attorney, Agent, or Firm* — Sheppard, Mullin, Richter & Hampton LLP

(57) ABSTRACT

Disclosed herein are systems methods for high content screening for microscope imaging. In some embodiments, the system comprises: a microscope; and a processor configured to implement: a slide loader module; a reference imager module; a slide imager module; a region of interest (ROI) finder module; a compare imager module; a calibrator module; and an image stitcher module.

23 Claims, 27 Drawing Sheets

(51) Int. Cl.
    *G06T 7/11*      (2017.01)
    *G06T 7/168*     (2017.01)
    *H04N 5/232*     (2006.01)
    *G02B 21/36*     (2006.01)
    *C12Q 1/6869*    (2018.01)
(52) U.S. Cl.
    CPC ............... *G06T 2207/20061* (2013.01); *G06T 2207/20221* (2013.01); *G06T 2207/30024* (2013.01)

(56) References Cited

U.S. PATENT DOCUMENTS

| | | | | |
|---|---|---|---|---|
| 2006/0045388 | A1* | 3/2006 | Zeineh | G02B 21/365 382/312 |
| 2006/0211044 | A1* | 9/2006 | Green | B01J 19/0046 435/7.1 |
| 2009/0006969 | A1* | 1/2009 | Gahm | G02B 21/367 715/732 |
| 2016/0011409 | A1* | 1/2016 | Oshima | H04N 5/23212 348/80 |

OTHER PUBLICATIONS

Boutros, et al., Microscopy-based high-content screening, Cell, Dec. 2015, 163(6):1314-1325.

Campos-Ortega, et al., The Embryonic Development of *Drosophila melanogaster*, Springer-Verlag Berlin Heidelberg, 1985, 237 pages (uploaded in two parts).

Hammonds, et al., Spatial expression of transcription factors in *Drosophila* embryonic organ development, Genome Biology, Dec. 2013, 14:R140.

Lein, et al., Genome-wide atlas of gene expression in the adult mouse brain, Nature, Jan. 2007, 445:168-176.

Levsky, et al., Gene expression and the myth of the average cell, Trends in Cell Biology, Jan. 2003, 13(1):4-6.

McNeill, et al., Mirror encodes a novel PBX-class homeoprotein that functions in the definition of the dorsal-ventral border in the *Drosophila* eye, Genes and Development, Apr. 1997, 11:1073-1082.

Pfeiffer, et al., Tools for neuroanatomy and neurogenetics in *Drosophila*, Proceedings of the National Academy of Sciences, Jul. 2008, 105(28):9715-9720.

Pollet, et al., An atlas of differential gene expression during early Xenopus embryogenesis, Mechanisms of Development, Mar. 2005, 122(3):365-439.

Preibisch, et al., Globally optimal stitching of tiled 3D microscopic image acquisitions, Bioinformatics, Apr. 2009, 25(11):1463-1465.

Schindelin, et al., Fiji: an open-source platform for biological image analysis, Nature Methods, Jun. 2012, 9(7), doi:10.1038/nmeth.2019.

Stuurman, et al., Computer control of microscopes using μManager, Current Protocols in Molecular Biology, Oct. 2010, pp. 14-20.

Tabara, et al. A multi-well version of in situ hybridization on whole mount embryos of Caenorhabditis elegans, Nucleic Acids Research, Jun. 1996, 24(11):2119-2124.

Weiszmann, et al., Determination of gene expression patterns using high-throughput RNA in situ hybridization to whole-mount *Drosophila* embryos, Nature Protocols, Apr. 2009, 4(5):605-618.

Zaharia, et al., Spark: cluster computing with working sets, Proceedings of the 2nd USENIX conference on Hot topics in cloud computing, p. 10-10, Jun. 22-25, 2010, Boston, MA.

Zanella, et al., High content screening: seeing is believing, Trends in Biotechnology, May 2010, 28(5):237-245.

* cited by examiner

| Image Properties | Source ROI Cutout | Tiled ROI Images | Stitched ROI Images |
|---|---|---|---|

Image Image(id=103, slideId=3, channel=0, slice=0, frame=0, position=102, acquisitionId=3), ROI ROI(id=31, imageId=103, x1=1980, y1=1960, x2=2740, y2=2832)

Channel 0, Slice 0, Frame 0
Go To Stage Position: (356.32,196221.04)
Return slide to loader

FIG. 2D

```
// SlideSurveyor PostProcessing
run("Bandpass Filter...", "filter_large=25 filter_small=15 suppress=Vertical tolerance=5 autoscale saturate");
run("Bandpass Filter...", "filter_large=25 filter_small=15 suppress=Horizontal tolerance=5 autoscale saturate");

// resize 0.5
run("Scale...", "x=0.5 y=0.5 width=4329 height=3629 interpolation=Bilinear average create");

// CustomMacroROIFinder Custom ROI Finding Macro
run("8-bit");
setAutoThreshold("IsoData");
setOption("BlackBackground", false);
run("Convert to Mask");
run("Gray Morphology", "radius=7 type=circle operator=dilate");
run("Analyze Particles...", "size=500-5000 exclude clear add in_situ");
```

*FIG. 6B*

HIGH CONTENT SCREENING WORKFLOWS FOR MICROSCOPE IMAGING

RELATED APPLICATIONS

The present application claims priority under 35 U.S.C. § 119(e) to U.S. Provisional Application No. 62/382,213, filed Aug. 31, 2016; the content of which is expressly incorporated herein by reference in its entirety.

STATEMENT REGARDING FEDERALLY SPONSORED R&D

This invention was made with government support under grant no. DE-AC02-05CH11231 awarded by the U.S. Department of Energy and by Grant Nos. R01GM097231 and R01GM076655 awarded by the National Institutes of Health. The government has certain rights in the invention.

BACKGROUND

Field

The present disclosure relates generally to the field of microscope imaging and more particularly to high content screening workflows for microscope imaging.

Description of the Related Art

Large-scale genome sequencing has rapidly facilitated the investigation and analysis of gene and protein functions and interactions. Efforts to interpret sequence data and to understand how it can be used to control cellular, tissue or organ system development have quickly revealed the limitations in the molecular understanding of multicellular organisms. Spatial gene expression can be important for understanding the events that are necessary for development of metazoans and large-scale studies are underway for a number of species. The existence of uniform cells or tissues has been questioned and their variance has been masked by single measurements.

SUMMARY

Disclosed herein are systems and methods for high content screening for microscope imaging. In one embodiment, the system comprises: a microscope; and a processor configured to implement: a slide loader module; a reference imager module; a slide imager module; a region of interest (ROI) finder module; a compare imager module; a calibrator module; and an image stitcher module. The slide loader module can be configured to control a robotic slide loader to load a slide. The reference imager module can be configured to capture a reference image of the slide for calibrating a slide position of the slide on a stage. The stage can be a motorized stage. The slide imager module can be configured to image the slide by capturing overlapping tiles of the slide. The region of interest finder module can be configured to determine at least one region of interest on the slide being imaged by analyzing the overlapping tiles of the slide. The compare imager module can be configured to capture an overlapping set of images centered around a user defined position of the slide. The calibrator module can be configured to match a position of the slide to the slide position. The image stitcher module can configured to stitch adjacent images. In another embodiment, the system comprises a microscope comprising a motorized stage, a camera and a robotic slide loader; a reference imager module for capturing, using the camera, a reference image of the slide on the motorized stage at a first stage position; a slide imager module for capturing, using the camera, a plurality of first modality, tiled images based on a first modality and a plurality of second modality images at a plurality of regions of interest based on a second modality; a region of interest finder module for determining the plurality of regions of interest at a plurality of image positions in the plurality of first modality, tiled images; a compare imager module for capturing, using the camera, a plurality of tiled comparison images around the first stage position; and a position calibrator module for determining an offset between the reference image and the plurality of tiled comparison images.

In one embodiment, the method comprises: obtaining a reference image of a calibration feature from a slide mounted on a microscope; obtaining a plurality of first modality images of the slide based on a first modality; determining a plurality of regions of interest at a plurality of image positions in the plurality of first modality images of the slide; obtaining a comparison image of the slide around the calibration feature; determining an offset between an image position of the calibration feature in the reference image and an image position of the calibration feature in the comparison image; updating the plurality of image positions based on the offset; and obtaining a plurality of second modality images of a plurality of regions of interest at the plurality of updated image positions based on a second modality.

Details of one or more implementations of the subject matter described in this specification are set forth in the accompanying drawings and the description below. Other features, aspects, and advantages will become apparent from the description, the drawings, and the claims. Neither this summary nor the following detailed description purports to define or limit the scope of the inventive subject matter.

BRIEF DESCRIPTION OF THE DRAWINGS

FIG. 2D shows an imaging result for one of the detected ROI with the left image at 5× magnification, the middle image at 20× magnification superimposed by relative position, and the right image at 20× magnification stitched with Fiji's algorithm.

FIG. 3A shows an image at 5× magnification at position defined by the user. FIG. 3B shows tiled images at 20× magnification around the original position of FIG. 3A. The automatically selected calibration image is framed. FIG. 3C shows edge images of FIGS. 3A-3B that were used for Generalized Hough Transform (GHT). FIG. 3D shows the position of the calibration image in the reference image shown with a box.

FIG. 5A shows the median and standard deviation of normalized values returned from each plugin at stage positions −50 µm to +50 µm. Values reported by the autofocus functions were normalized as z-scores (centered to have mean 0 and scaled to have standard deviation 1). FastFFT is shown on the top, J&M is shown in the middle, and OughtaFocus is shown at the bottom. The stage positions for all three plugins were centered around the best value return for FastFFT. J&M showed the largest variance. FIG. 5B shows a box plot showing the execution times for the three plugins for the 100 sampled stage positions. FIG. 5C shows early blastoderm embryo (left) and late embryo (right) showing the highest scoring focal planes for FastFFT (top) compared to OughtaFocus and J&M (bottom). Results show little discernible difference for the early embryo but a focal plane in the middle of the embryo for FastFFT compared to a focal plane on the surface for J&M.

FIGS. 6A-6E show a CustomMacroROIFinder module for *Drosophila* imaging. FIG. 6A shows a configuration dialog with text box for custom macro. FIG. 6B shows codes of a macro used for *Drosophila* imaging workflow. FIG. 6C shows an excerpt of the stitched slide from SildeSurveyor. FIG. 6D shows the image in FIG. 6C after applying FFT Bandpass filter. FIG. 6E shows the result after thresholding, morphology and particle detection.

FIG. 7A shows a configuration dialog with the workflow arranged in a tree-like structure. Child modules are displayed a higher level of indentation than the parent modules. The workflow execution starts at Phase 1 or 2 entry points and stops when it reaches a point with no further child modules. FIG. 7B shows a schematic representation of the workflow. Phase 1 of the workflow loads a slide (the SlideLoader module), takes a reference image for calibrating the slide position on the stage (the refImager module), images the slides in overlapping tiles (the SlideImager module), detects ROIs and stops. Phase 2, configured as second entry point, loads the same slides a second time (the SlideLoader module), calibrates the position list by taking images around the reference images and finding a matching position (the compareImager module), images the ROIs from the first workflow (the SlideImager module) and, if necessary, stitches adjacent images (the SlideStitcher module).

FIG. 9A shows a schematic view of the genomic region of mirr, the positions of the five CRM constructs, GMR34C02, GMR34C05, GMR33E04 intergenic 5' of the mirr transcripts (GMR34C02, GMR34C05 now span two adult male expressed predicted non-coding transcripts) and GMR33C10 and GMR33B03 are intronic residing in the $2^{nd}$ and third intron respectively, and the mirr transcripts, RA, RB and RC. FIG. 9B shows images for embryos hybridized with Gal4 or mirr probes at stage ranges 4-6, 9-10 and 13-16. All embryos are shown from a lateral view anterior to the left. The arrowheads point to the wild-type and GMR33E04 expression in the foregut anlage in situ nascendi (AISN) (stage ranges 4-6) and the wild type and GMR34C02 proventriculus (stage range 13-16). Eight images (marked with an asterisk) are composite stitched images from overlapping tiled ROIs.

FIG. 10A shows GMR33E04 and wild-type mir expression at stages 4-6 from ventral. The photographs show that the wild-type exhibited a continuous pattern whereas GMR33E04 had two smaller expression domains at the boundaries of the wild-type gene expression. FIG. 10B shows the GMR33C10 expression at stages 4-6 continues in a segmentally repeated pattern at stages 7-8.

FIG. 11A shows basic configuration options for the hardware. For robotic loading of slides, the stage is moved to a position matching the slide loader and the position can be defined here. FIG. 11B shows the definition for the metadata of the slide pool. Each slide in the slide loader (a row in the dialog) was located in a cartridge and a position in that cartridge and can be assigned with a descriptive entry.

FIG. 14A shows an image at 5× magnification with embryos. FIG. 14B shows edge detection. FIG. 14C shows detected ROI as black object masks.

DETAILED DESCRIPTION

Figure 1A:
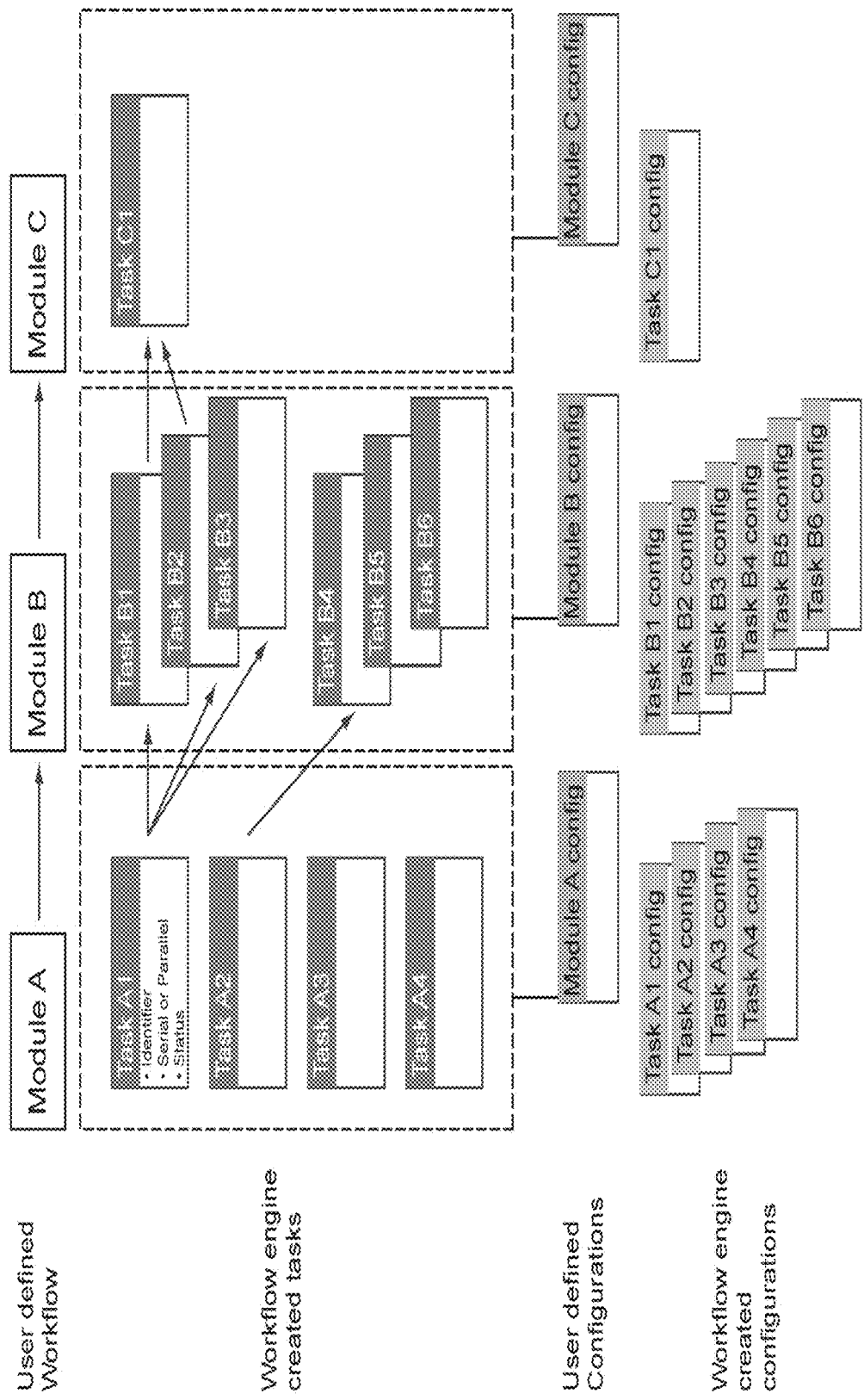
FIG. 1A shows a OpenHiCAMM data model. Shown are three modules, labeled A, B, C with module specific tasks (labeled A1, A2, and A3 for module A, etc.), module configurations and task configuration entries. The user defines the workflow and the module configurations, the workflow engine creates the tasks and the task configurations (left).

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

Disclosed herein are systems and methods for high-content image acquisition of biological samples. In one embodiment, a high-content image acquisition system can include, or be in communication with, a microscope and a camera of the microscope (or a camera attached to the microscope). The system can control the camera to capture images of a number of slides during a first pass. For example, the camera can capture an image for each slide. The images captured can be lower in resolution (as compared to images captured during a second pass). The system can receive the images captured from the camera. The system can include, or be in communication with, a slide loader for holding the slides. Accordingly, the system can be used to capture images of a number of slides automatically. A slide can contain a sample of interest such as *Drosophila* embryos, sample slides (e.g., slides containing sections of a brain), cells (e.g., cells infected by virus such as the Zilka virus, cancer cells, healthy cells, cells in different cell cycles, stem cells,), and tissues. For example, the maturation of human pluripotent stem cells (hPSCs) into embryoid bodies, neuroectoderm, expanded neuroepithelium, and cerebral tissue can be imaged.

The system can analyze the images captured to identify regions of interest (ROIs) on the slides. For example, if a slide contains *Drosophila* embryos, the system can implement computer vision methods to identify the locations of the embryos. Based on the analysis, high resolution images of the regions of interest can be captured. The system can control a slide loader to load a slide onto a stage of a microscope. The system can record the identity of the slide, or the slide can include a label for identification. The system can control the stage to move the slide such that images of the ROIs are captured. The images of the ROIs can be stitched or combined together to create a final high resolution image of the ROIs. For example, a final high resolution image of an embryo may be stitched together from a number of high resolution images showing the embryo. Advantageously, the system can generate high resolution images of ROIs in a short period of time because high resolution images of non-ROIs are not captured.

The system can be flexible to control different types of microscopes, cameras, slide loaders, and stages. The microscopes used during the first pass and the second pass may be the same or different. For example, microscopes can be an optical microscope such as a differential interference contrast microscope. The microscope used for the first pass may have lower resolution, and the microscope used for the second pass may have higher resolution. As another example, the microscope used for the first pass may be a differential interference contrast microscope, and the microscope used for the second pass may be a fluorescent microscope or a confocal microscope (e.g., a three-dimensional confocal microscope). Advantageously, the system can control multiple microscopes. For example, the system can use one of three microscopes (e.g., a high magnification differential interference contrast microscope, a fluorescent microscope, or a confocal microscope) for the second pass.

High-content image acquisition may be used in cell culture requiring high-density samples, complex hardware and preset imaging modalities. Disclosed herein are systems and methods for high content screening for microscope imaging. In some embodiments, the systems and methods can implement or be implemented as a software package that provides a flexible framework for integration of generic microscope associated robotics and image processing with sequential workflows. For example, the software package can be referred to as OpenHiCAMM. The OpenHiCAMM software has numerous applications. For example, *Drosophila* embryos can be imaged to detect the embryos at low resolution, then re-imaging the detected embryos at high resolution, suitable for computational analysis and screening.

High content screening of cells can be used for drug screening. However, there is a tradeoff between the depth and the size of the field of view with existing single pass imaging technologies, which may be limited to imaging single cells. The OpenHiCAMM software can be used for imaging complex biological samples with its automated or semi-automated multi-pass imaging technology. This multi-pass, automated or semi-automated imaging technology allows lenses and illumination to be changed during the different passes of imaging the same sample. Different microscopes can be used for different passes of imaging the same sample. In one implementation, the OpenHiCAMM software implements a generalizable workflow engine that is capable of hardware interaction and operation and software processing. The workflow implemented by the OpenHiCAMM software can improve on the human imaging workflow to image, detect objects, change microscopes and re-image previously found objects, such as *Drosophila* embryos.

In one embodiment, the OpenHiCAMM software can be used for high-content screening (HCS) for cell culture imaging, pharmaceutical drug discovery, genome-wide RNA interference (RNAi) and CRISPR. The software can control a microscope and associated robotics to scan multi-well plates and slides. The OpenHiCAMM software can be customized for and used in conjunction with different robotics, microscopes and software. For example, the OpenHiCAMM software can be used with existing microscope systems or microscope systems developed in the future. Imaging can occur in multiple passes, minimizing the compromise between resolution and field depth. For example, for single cell samples, a tradeoff between resolution and cell density can be minimized. Imaging of transient transfections experiments can be achieved with the OpenHi-CAMM software, even if the transient transfections do not have sufficient cell transfection density. For larger samples, such as histological sections, organoids, or whole mount samples of model organisms or tissues, tiling of a specimen at low resolution or placing a specimen at a predefined position may be unnecessary.

The systems and methods disclosed herein can be implemented as high-throughput imaging software. In some implementations, the software can be tailored to image samples that require multi-step workflows contingent on image analysis and multiple imaging modalities. The software, OpenHiCAMM (Open Hi Content Acquisition for μManager), is designed to control optical microscopes and also interface with an automated slide loader to perform fully automated HCS. OpenHiCAMM can be implemented as one or more modules for the popular Open Source bioimage analysis package from Fiji and microscope hardware control μManager. For example, OpenHiCAMM can utilize μManager for its broad support of microscopes, components and cameras and its flexible slide acquisition. For advanced image analysis, Fiji's software components may be used.

Figure 1B:
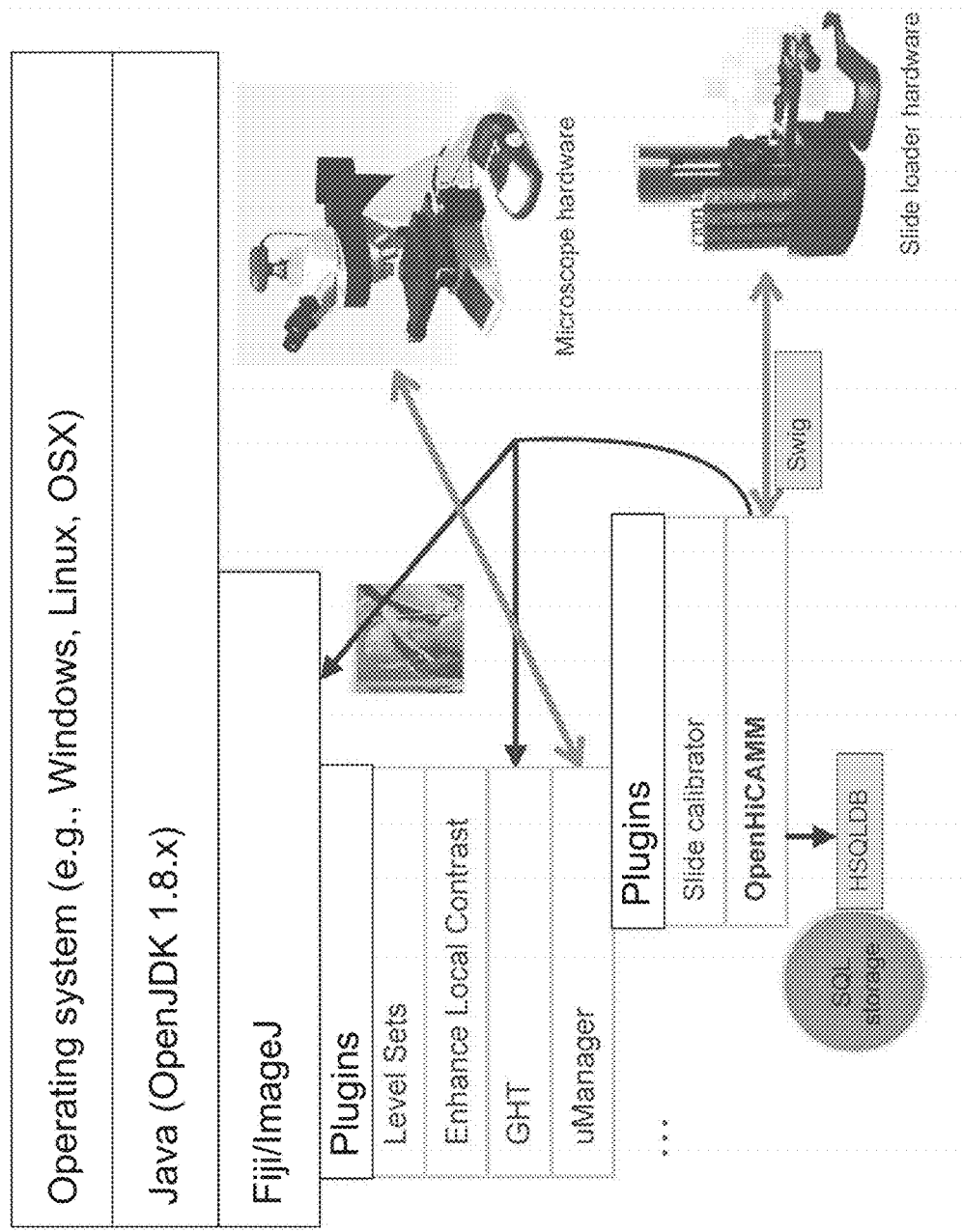
FIG. 1B shows dependencies of components in an exemplary imaging system.
Figure 2A:
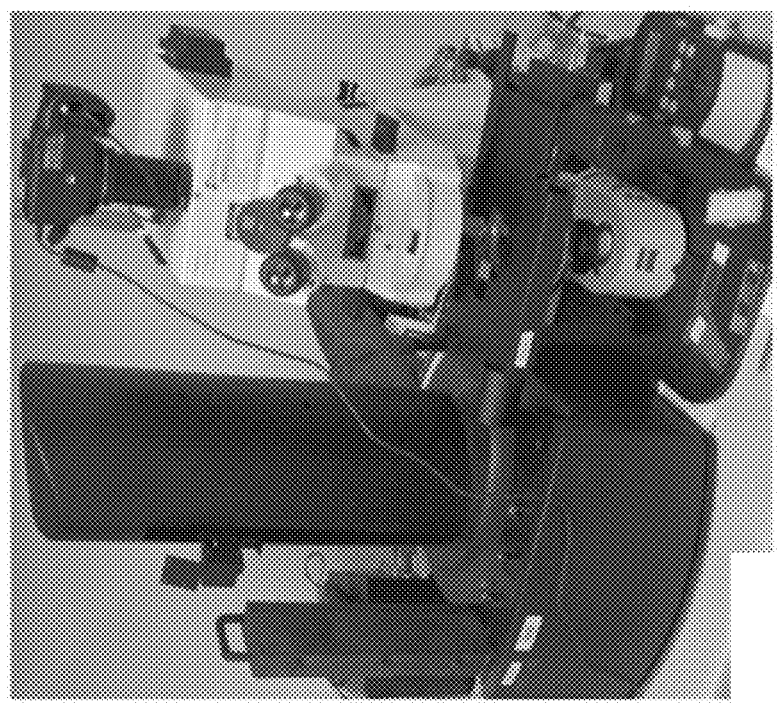
FIG. 2A shows a microscope setup with a microscope and automated slide loader on the left.
Figure 2B:
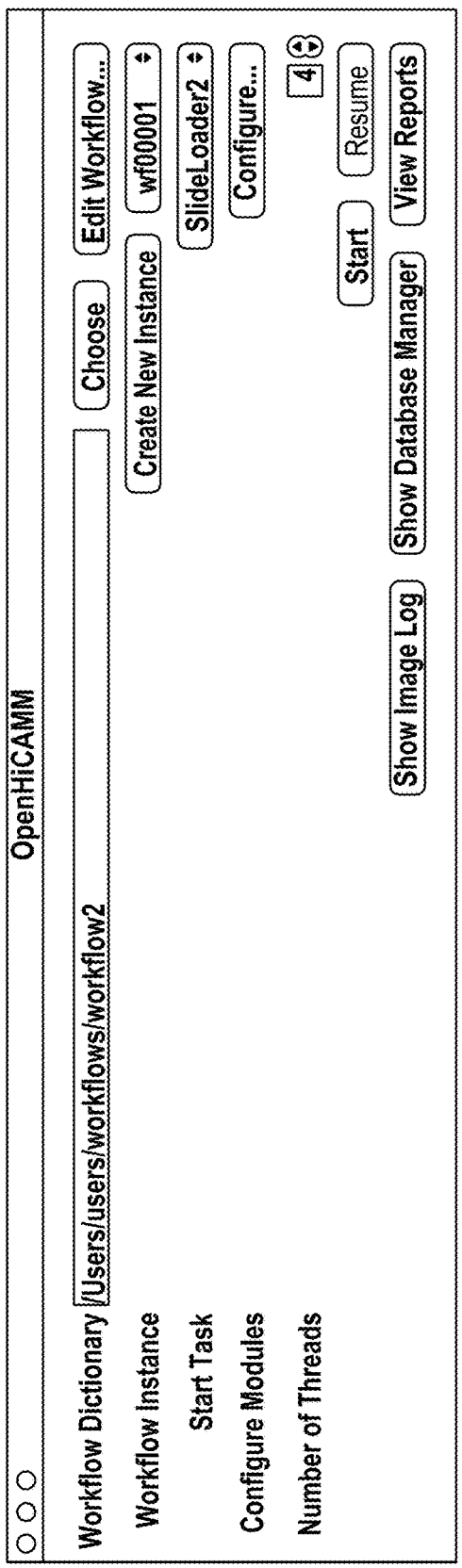
FIG. 2B shows a main dialog for OpenHiCAMM, showing the current selection of the storage location, a currently selected workflow instance and various configuration and debug options.
Figure 2C:
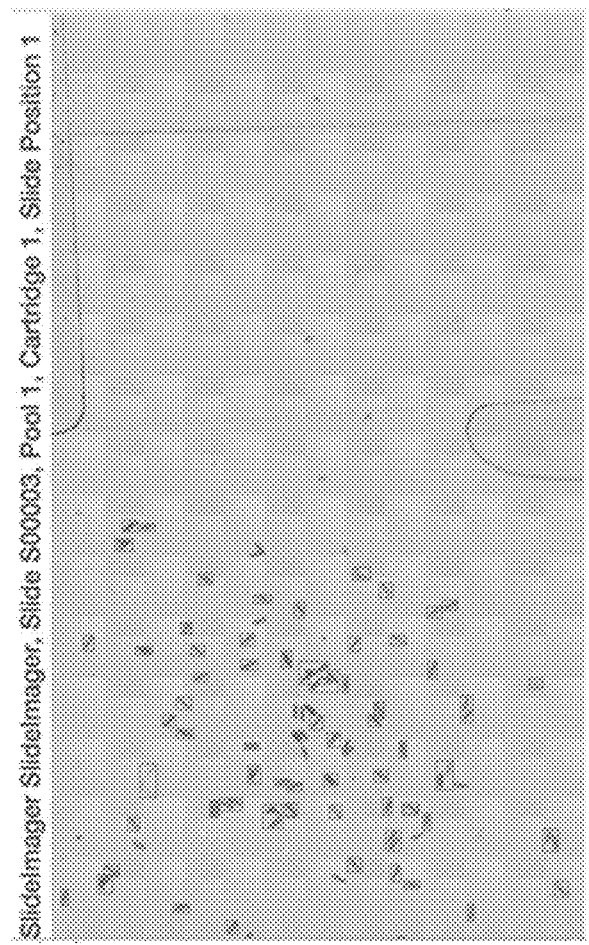
FIG. 2C is an overview of a slide, stitched by stage position and the detected ROI (red boxes).

The core of OpenHiCAMM can include a sophisticated workflow manager that executes modules operating the robotic hardware and performs imaging and processing of data (Table 1, FIGS. 1A-1B). Table 1 includes a list of implemented modules and their functions for OpenHiCAMM. The workflow manager executes microscope dependent modules sequentially and computational processing modules in parallel. OpenHiCAMM uses an integrated SQL database engine for persistent storage of workflow setups, module configurations and for recording the completed tasks, thus allowing for recovery from operational hardware problems, stopping or resuming interrupted workflows. Both the database files and the image files, in standard μManager file and directory format, are stored in a user selectable local or remote disk destination (FIG. 2B).

allowing for loading and imaging slides repeatedly. In some embodiments, changing image modalities and manual adjustments of the microscope between each imaging pass can be implemented. Loading slides multiple times may result in possible offsets to the slide position on the stage. To correct for these offsets, modules for calibrating the stage position using the location invariant edge between the frosted end and the adjacent transparent glass in commercially available slides can be utilized (FIGS. 3A-3D and 4).

Figure 5A:
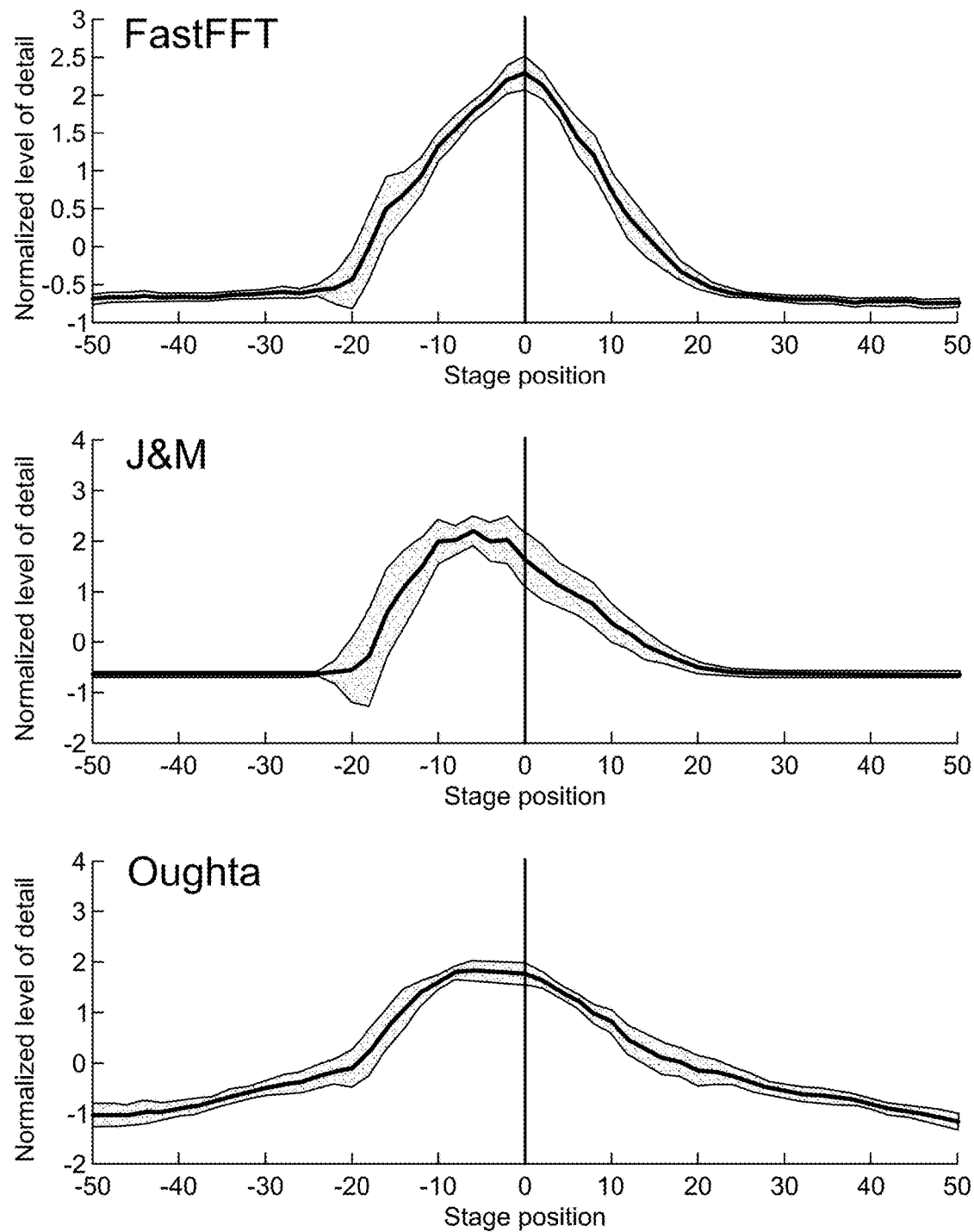
FIGS. 5A-5C show autofocus performance of FastFFT compared to µManager's J&M and OughtaFocus function (at default setting).
Figure 5B:
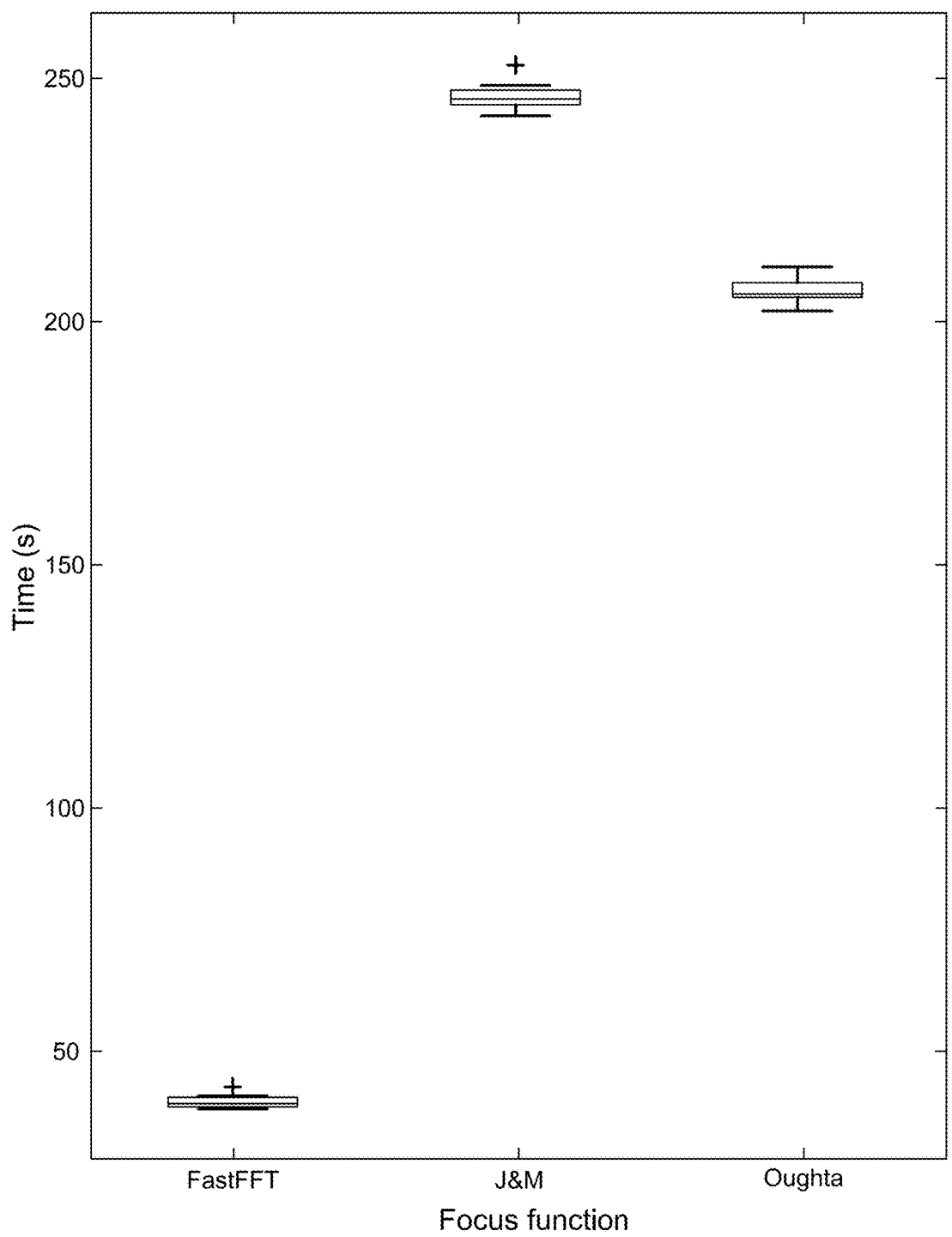
Figure 5C:
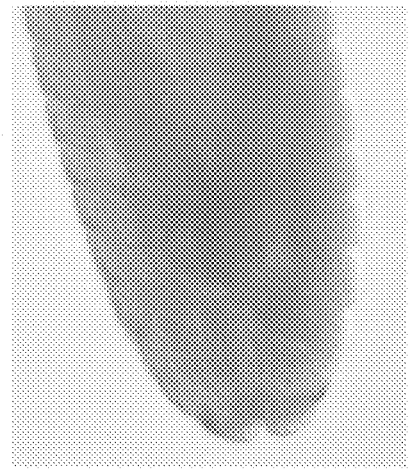
Figure 5C:
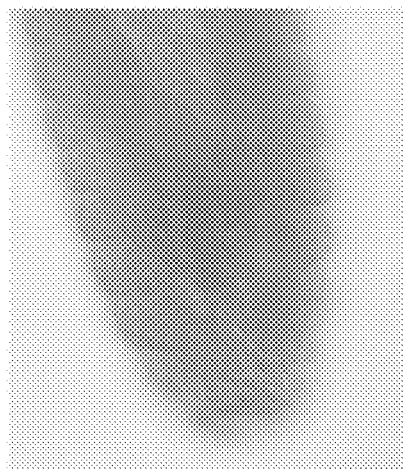
Figure 5C:
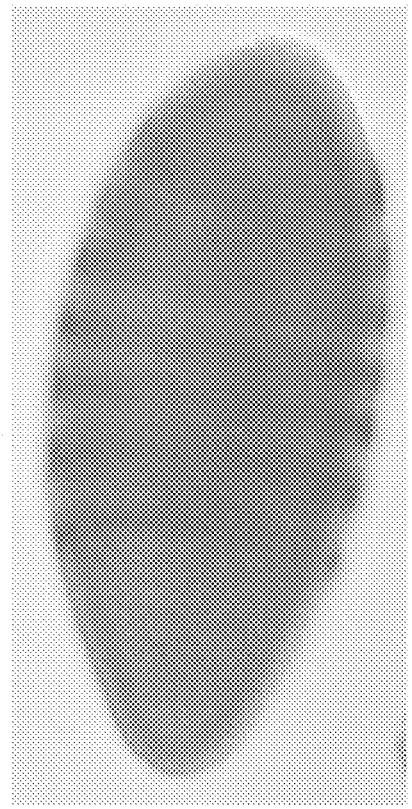
Figure 5C:
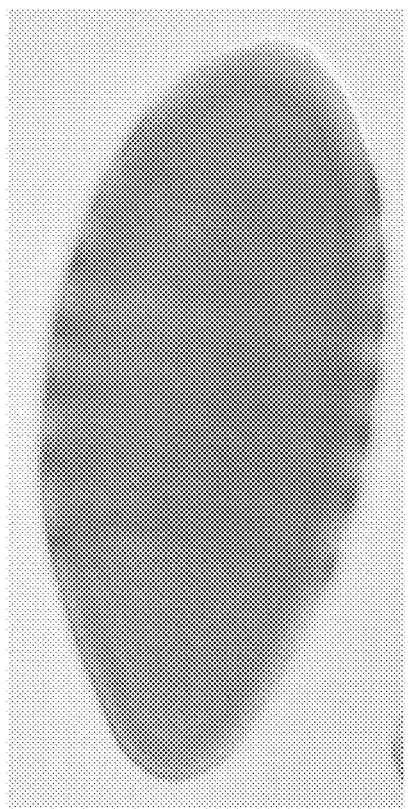
Figure 6A:
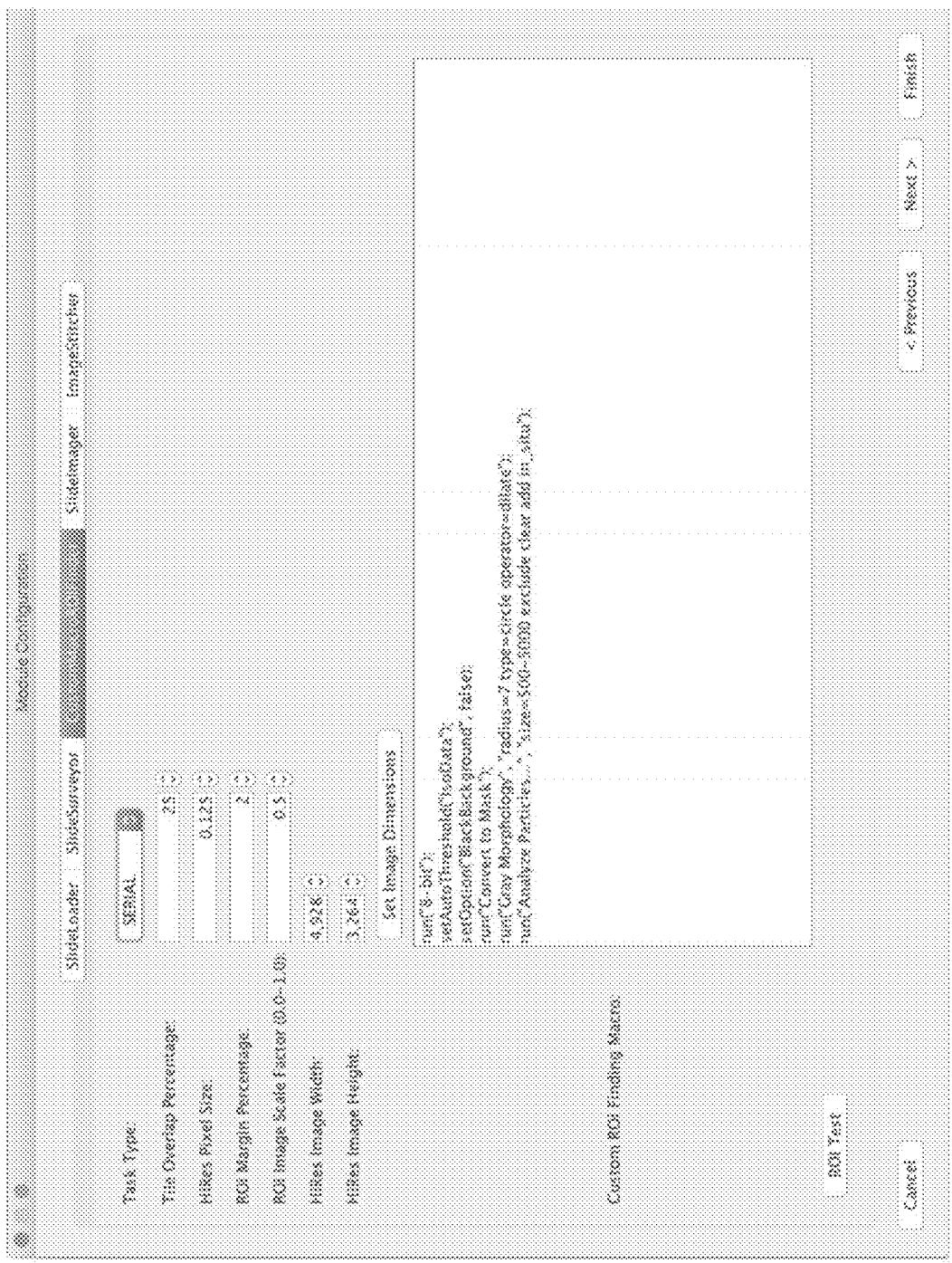
Figure 6E:
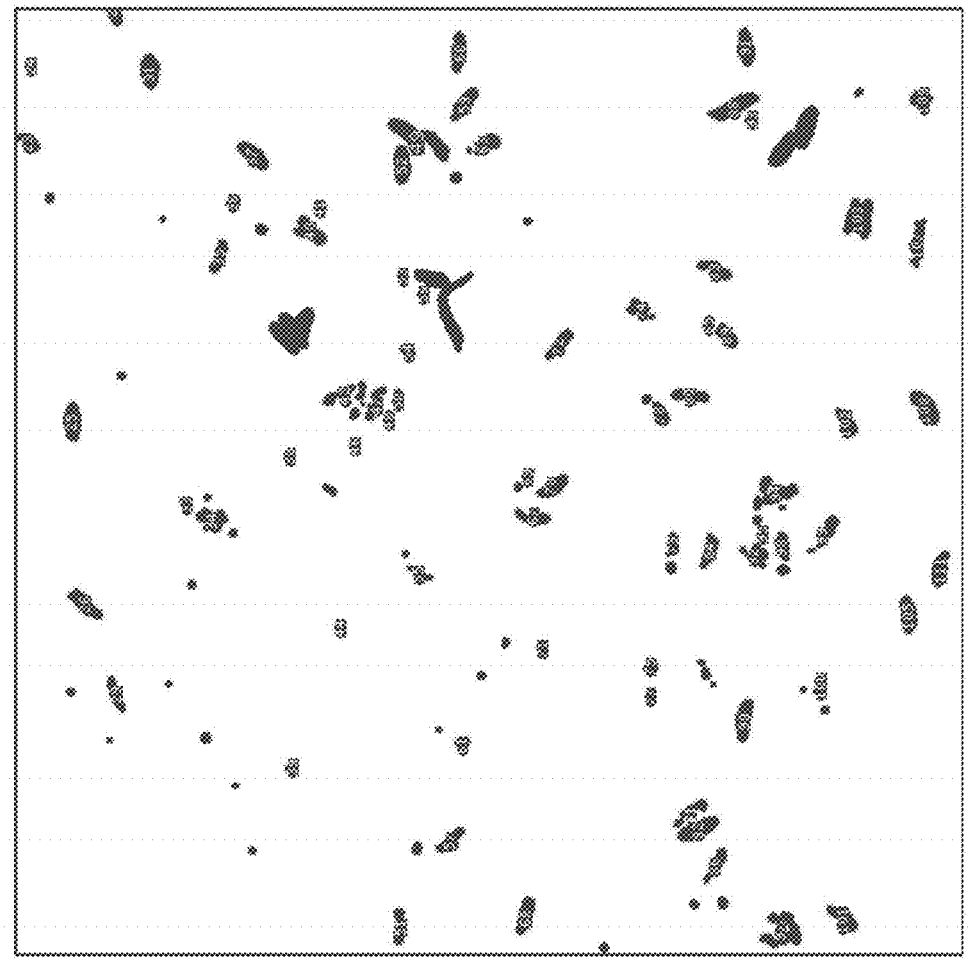
Figure 6C:
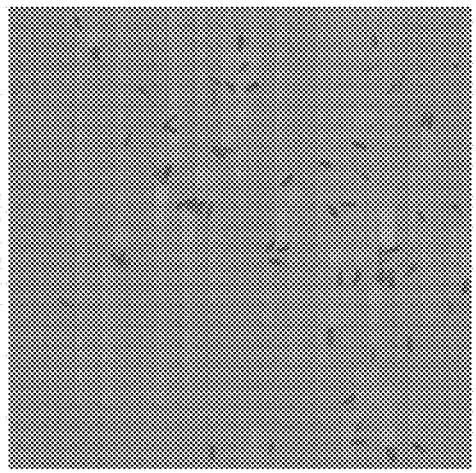
Figure 6D:
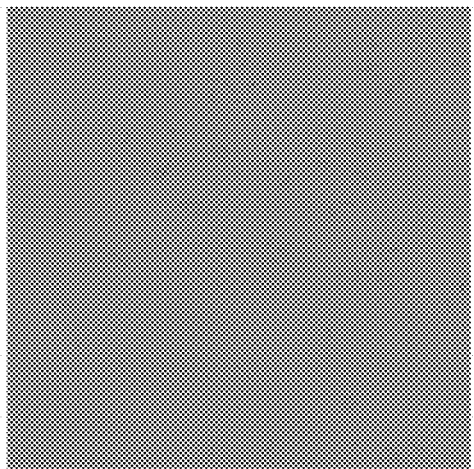

Imaging of the slide can be performed by the SlideImager module, which is a wrapper for μManager's Multi-D acquisition and thus able to use all capabilities of μManager, including selectable light filters and stacks along the Z-axis. If an area exceeds the size of a single camera snapshot, multiple tiled images are acquired and post-processed with Fiji image stitching to assemble a composite image (FIG. 2D). To increase the acquisition rate, a fast custom autofocus plugin can be used (FIGS. 5A-5C).

A workflow and modules can be implemented that are optimized for imaging of slides containing whole mount *Drosophila* embryos with gene expression patterns detected by in situ mRNA hybridization. The systems and methods disclosed herein can control a microscope platform with a slide loader, a motorized microscope, a camera, and/or a motorized stage. For example, embodiments of the OpenHiCAMM software can control a HCS microscope platform with a Prior PL-200 slide loader, a Zeiss Axioplan 2 motorized microscope, a Nikon DSLR D5100 camera and a Prior motorized stage (FIG. 2A). DIC microscopy can be used for capturing both probe staining and sample morphology in a single image, thus making it particularly well suited to high throughput analysis of tissue or organisms and for studying ontogeny, such as a developing *Drosophila* embryo.

Figure 7A:
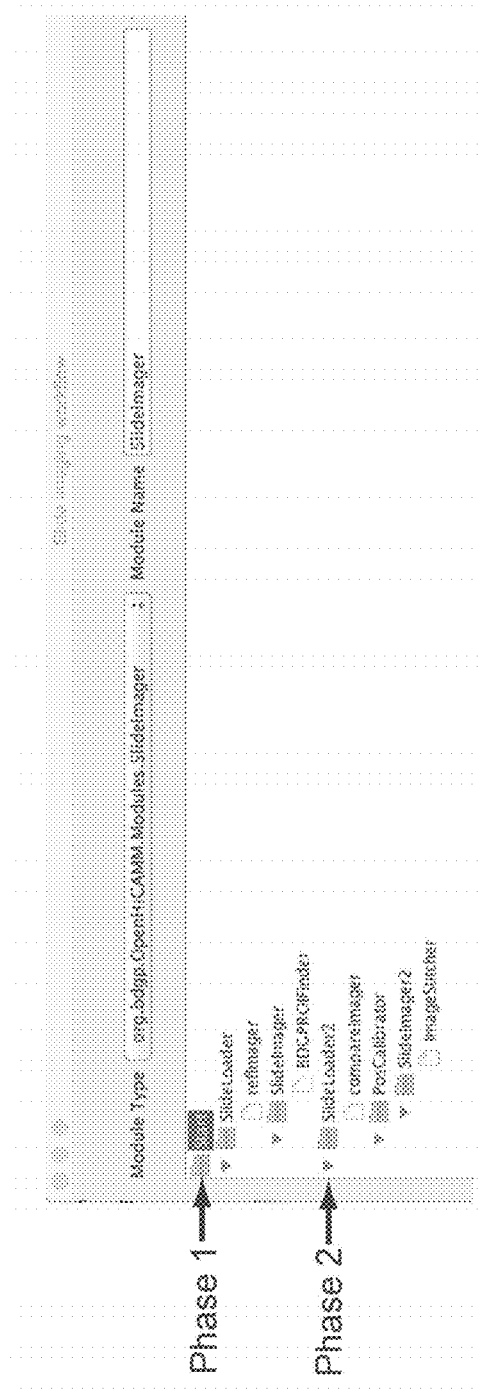
FIGS. 7A-7B show a workflow for *Drosophila* imaging. Shown is the 5×/20× magnification configuration used for imaging *Drosophila* embryos.
Figure 7B:
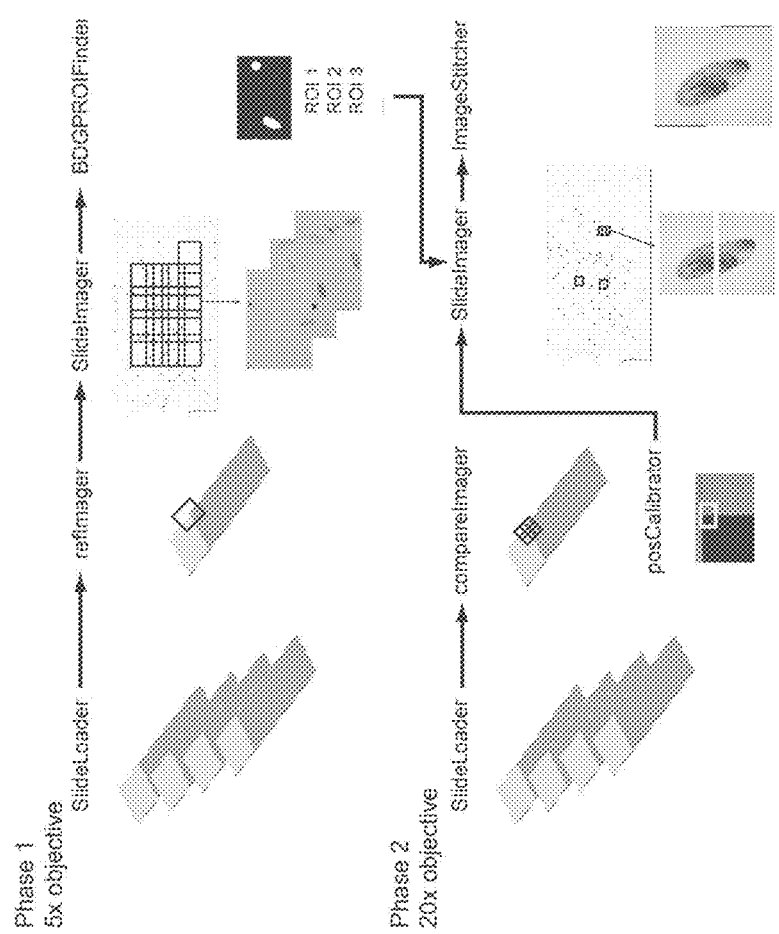

In some embodiments, the workflow to image *Drosophila* embryos can include two imaging modalities (FIGS. 7A-7B). For the first pass (Phase 1), the microscope can be

TABLE 1

List of implemented modules and their functions for OpenHiCAMM.

| Module name | Module function | Hardware control |
|---|---|---|
| SlideLoader | Slide management, loading slides or prompting user to place slide on stage | optional robotic slide loader |
| SlideImager | Imaging of a slide | Robotic stage, optional Z-axis and illumination/filters |
| SlideSurveyor | Fast low resolution imaging of a slide using a live video feed from the | Robotic stage |
| BDGPROIFinder | Region of interest detection | none |
| CustomMacroROIFinder Finder | Region of interest detection with Fiji/ImageJ macros | |
| ImageStitcher | Registration and stitching of adjacent images | none |
| refImager | Imaging a reference position | Robotic stage |
| compareImager | Capturing set of images, such as tiled around reference position defined in the refImager module | none |
| PosCalibrator | Computational comparison of reference images and comparison images and adjustment of position list. | none |

To automate slide handling for HCS, a slide management module, the SlideLoader module, can be used to track the slides and either interface with a hardware slide loader or, for semi-automatic imaging without the slide loader, prompt the user to place the slide on the stage. The SlideLoader module can be used multiple times in the same workflow calibrated for a 5× objective. The workflow can be run to first image manually selected areas of the slide occupied by the cover slip as tiled images, followed by an image analysis module to identify embryos on that area of the slide. After completion of the first pass, the microscope can be adjusted (manually or automatically) for a 20× objective and resume the workflow a second entry point (Phase 2). The workflow can re-load the slides and re-images detected embryos at higher magnification.

Figure 4:
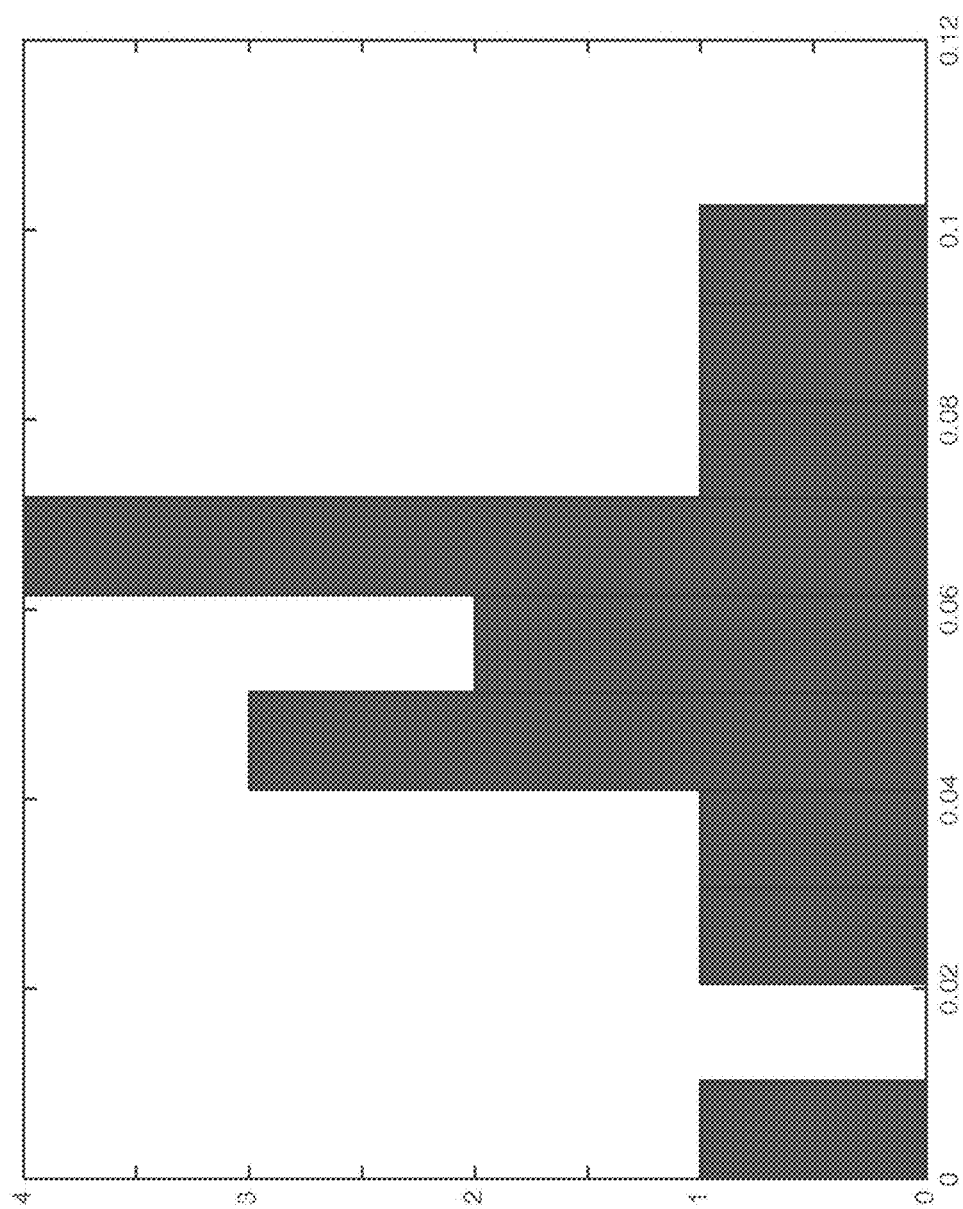
FIG. 4 shows precision of detecting same objects after calibrating slides. Histogram depicts the Euclidean distance between the positions of 10 objects in µm.

In some embodiments, the performance of the systems and methods disclosed herein can be accessed with respect to the precision and speed of the imaging process, for example. Imaging objects on slides with a permanent marker can be created, the imaging workflow performed, and the objects superimposed (e.g., manually). In some embodiments, the average displacement can be 0.059 µm, about 1.5% of the image at 20× magnification (FIG. 4). In some embodiments, on average, the tiling at 5× can take 2.3 seconds/image and the 20× images, including a focus step each 25 images, 12 seconds each. At 5× magnification, the slides can be covered with 200-300 tiles, resulting in a rate of about 12 minutes per slide. The second phase high resolution imaging with 20× magnification may take about 20 minutes for each 100 detected objects. Imaging the slide with high resolution at 20× magnification may take over 3000-6500 images. Thus, with approximately 300 embryos per slide, the imaging strategy can achieve a more than 10 fold increase in speed compared to prior imaging strategies.

The systems and methods disclosed herein (e.g., Open-HiCAMM) can autonomously complete an HCS experiment. For example, the workflow can be used to image 95 slides made from a 96-well plate experiment. For the low-resolution pass, a slide area with 180 tiles may be selected. Low-resolution imaging may be completed in eight minutes per slide and yielded 26-751 objects (continuous areas containing one or multiple embryos) per slide. In the second pass, high-resolution images for embryos can be obtained with imaging times ranging from 39 minutes (61 objects with 119 images) to 113 minutes (334 objects within 573 images) for 90% of the slides excluding those at the tails of the distribution (too few or too many embryos per slide, FIG. 8).

For cases that rely only on high-resolution imaging, an additional module, the SlideSurveyor module, was developed. The SlideSurveyor module takes advantage of the camera video feed to rapidly image the slide from a live view of the sample. For example, objects can be imaged and reimage with the SlideImager module. All steps can use the same imaging modality, thus limiting alignment problems and user intervention from repeated slide loading. Using SlideSurveyer for Phase 1 at 20× magnification resulted in 20 minutes per slide, while avoiding slide reloading and changing the objective.

Advantageously, the systems and methods disclosed herein can be robust and flexible and can be easily adapted and extended to other high throughput robotics tasks that are increasingly common in modern biology, making the systems and methods uniquely positioned to provide a foundation for sophisticated high throughput screens.

Figure 17:
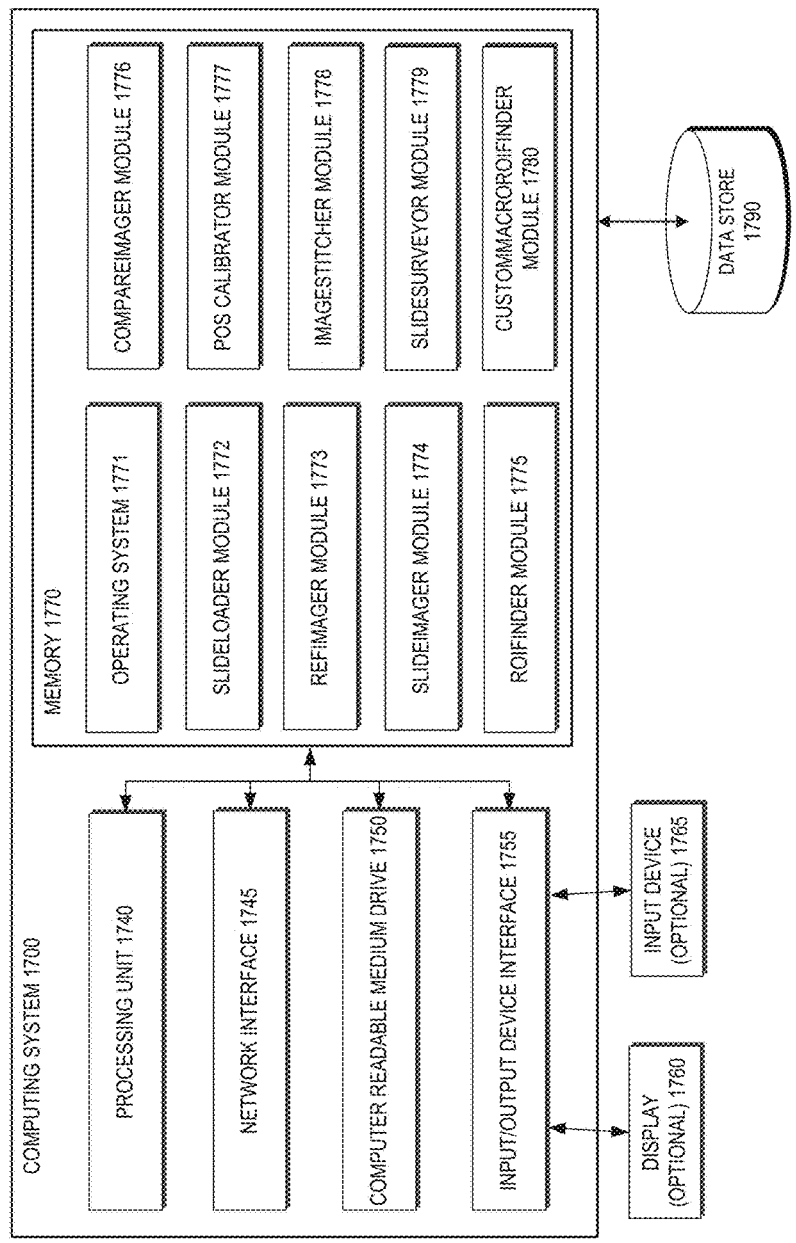
FIG. 17 depicts a general architecture of an example computing device configured to perform high content screening for microscope imaging.

FIG. 17 depicts a general architecture of an exemplary computing system 1700 configured to learn a machine learning model and generate a prediction result using the model. The general architecture of the computing device 1700 depicted in FIG. 17 includes an arrangement of computer hardware and software components. The computing system 1700 may include many more (or fewer) elements than those shown in FIG. 17. It is not necessary, however, that all of these generally conventional elements be shown in order to provide an enabling disclosure. As illustrated, the computing system 1700 includes a processing unit 1740, a network interface 1745, a computer readable medium drive 1750, an input/output device interface 1755, a display 1760, and an input device 1765, all of which may communicate with one another by way of a communication bus. The network interface 1745 may provide connectivity to one or more networks or computing systems. The processing unit 1740 may thus receive information and instructions from other computing systems or services via a network. The processing unit 1740 may also communicate to and from memory 1770 and further provide output information for an optional display 1760 via the input/output device interface 1755. The input/output device interface 1755 may also accept input from the optional input device 1765, such as a keyboard, mouse, digital pen, microphone, touch screen, gesture recognition system, voice recognition system, gamepad, accelerometer, gyroscope, or other input device.

The memory 1770 may contain computer program instructions (grouped as modules or components in some embodiments) that the processing unit 1740 executes in order to implement one or more embodiments. The memory 1770 generally includes RAM, ROM and/or other persistent, auxiliary or non-transitory computer-readable media. The memory 1770 may store an operating system 1771 that provides computer program instructions for use by the processing unit 1740 in the general administration and operation of the computing device 1700. The memory 370 may further include computer program instructions and other information for implementing aspects of the present disclosure. For example, in one embodiment, the memory 1770 includes a SlideLoader module 1772, a refImager module 1773, a SlideImager module 1774, and a ROIFinder module 1775. The memory 1770 may additionally or alternatively include a compareImager module 1776, a posCalibrator module 1777, and an ImageStitcher module 1778. The memory 1770 can also include a slideSurveyor module 1779 and a CustomMacroROIFinder module 1780 In addition, memory 1770 may include or communicate with data store 1790 and/or one or more other data stores that stores raw image data and imaging results. In one embodiment, the modules 1772-1780 in the memory 1770 can control components of a microscope or components associated with a microscope, such as a robotic slide loader, a motorized stage, and a camera.

EXAMPLES

Example 1

Whole Mount *Drosophila* Embryos Imaging

This example shows using OpenHiCAMM to perform whole mount *Drosophila* embryo imaging.

A workflow and related modules were developed and optimized for imaging slides containing whole mount *Drosophila* embryos with gene expression patterns detected by in situ mRNA hybridization. A HCS microscope platform with a Prior PL-200 slide loader, a Zeiss Axioplan 2 motorized microscope, a Nikon DSLR D5100 camera and a Prior motorized stage were assembled (FIG. 2B). DIC microscopy was used for capturing both probe staining and sample morphology in a single image, thus making it particularly well suited to high throughput analysis of tissue or organisms and for studying ontogeny such as a developing *Drosophila* embryo. The workflow was designed to image *Drosophila* embryos with two imaging modalities (FIGS. 7A-7B). For the first pass (Phase 1), the microscope was calibrated for a 5× objective. The workflow was run to first image manually selected areas of all slides as tiled images, followed by an image analysis module to identify embryos on the slide. After completion of the first pass, the microscope was manually adjusted for a 20× objective and started the workflow at the second entry point (Phase 2). The workflow re-loaded the slides and re-images detected embryos at higher magnification. At 5× magnification, the entire slide can be imaged with 200-400 images, whereas at 20× it would take over 16 times as many images (3000-6500). Thus, with approximately 300 embryos per slide, this imaging strategy can achieved a more than 10 fold increase in speed in comparison to prior systems.

To assess the performance, precision and speed of the imaging process imaging objects on slides with a permanent marker were manually created, the imaging workflow was performed and the objects manually superimposed. The average displacement was 0.059 µm, about 1.5% of the image at 20× magnification (FIG. 4). On average, the tiling at 5× took 2.3 seconds/image and the 20× images, including a focus step each 25 images, 12 seconds each. At 5× magnification, the slides can be covered with 200-300 tiles, resulting in a rate of about 12 minutes per slide. For each 100 detected objects, the 20× magnification imaging takes about 20 minutes. The choice of an inexpensive DSLR camera left room for improvement with faster imaging hardware.

To demonstrate OpenHiCAMM's ability for autonomously completing an HCS experiment, the workflow was used to image 95 slides made from a 96-well plate experiment. For the low-resolution pass, a slide area with 180 tiles was selected. Low-resolution imaging completed in eight minutes per slide and yielded 26-751 objects (continuous areas containing one or multiple embryos) per slide. In the second pass, high-resolution images for embryos were obtained with imaging times ranging from 39 minutes (61 objects with 119 images) to 113 minutes (334 objects within 573 images) for 90% of the slides excluding those at the tails of the distribution (too few or too many embryos per slide, FIG. 8).

Altogether, these data show using OpenHiCAMM to automatically perform whole mount *Drosophila* embryos imaging.

Example 2

OpenHiCAMM Workflow Manager, Data Model and Module Management

This example shows the OpenHiCAMM workflow manager, data model and module management.

OpenHiCAMM Workflow Manager, Data Model and Module Management

OpenHiCAMM was written in the Java 1.8 programming language as a plugin for µManager 1.4.x. While compatible with the basic ImageJ and µManager distribution, for image processing, it required the extended and standardized plugin selection provided by Fiji. At its core was a custom workflow manager providing following functionality: 1. A common interface for modules implementing either hardware control or image processing tasks; 2. Configuration of a modularized workflow and module specific parameters; 3. Resolving dependencies and ordered execution of the modules; 4. Metadata and image storage management; 5. Response to events from the hardware; and 6. A graphical user interface for designing workflows, configuring storage and modules and starting/stopping and resuming workflows.

OpenHiCAMM itself was platform agnostic but µManager hardware support depended on the operating system. The C++ code was developed and tested for the Prior PL200 slide loader hardware adapter on Macintosh OSX 10.10 (or newer) and under Linux.

The source code is available on Github (https://github.com/bdgp/OpenHiCAMM).

Data Model

The OpenHiCAMM workflow engine in one implementation managed two types of data, a set of execution tasks and the module and task configurations (FIG. 1A).

Execution Tasks:

Each task represented a single unit of work. The purpose of a task was 1) to allow the system to schedule module executions and 2) to provide a record of successful or unsuccessful module completion. Tasks were connected to each other using a directed acyclic graph. A workflow task may be started once all of its parent tasks have completed successfully. Workflow modules may tag tasks as serial or parallel. Serial tasks were completed in sequential order, and were suitable for hardware dependent tasks such as slide loading and imaging. Parallel tasks can be run simultaneously and were suitable for image processing or analysis. Each task consists of a unique task identification number, its current status, and its associated module. Tasks were connected together in parent-child relationships. The task workflow can be similar to the concept of a data dependency graph used in some workflow execution systems.

Workflow Module and Task Configurations:

Metadata for configurations were stored as key-value pairs. Workflow module configurations were parameters set by the user and can be accessed by all tasks in the module. Module configurations were used for configuring parameters that apply to all tasks within the module. Task configurations apply to each task individually. Task configurations were not manually entered by the user, but were generated by the module. The task configuration was used to store information about which item of work each task was to perform. For example, the SlideLoader task configuration stored the identification and location for the slide to load, the SlideImager task configuration stored the identification of the image to be acquired by that task.

Images were part of the task data and not explicitly handled. OpenHiCAMM directs the µManager acquisition engine to store images in its native format to a workflow dependent location and tracks imaging through the task sets.

Altogether, these data show the OpenHiCAMM workflow manager, data model and module management.

Example 3

Workflow Implementation and API

This example shows a workflow implementation and API of OpenHiCAMM.

Workflow Implementation and API

System Architecture

The OpenHiCAMM workflow engine was designed to store its data in a SQL database backend. In one version, HSQLDB (http://hsqldb.org) was implemented as database backend. HSQLDB was chosen because it was implemented in pure Java and can be distributed as a cross-platform JAR file, making installation using the Fiji update manager much easier.

Each workflow module can create a configuration entry and one or more tasks. Upon invocation of a configured workflow, a new workflow instance with a task list was generated, tasks linked as an acyclic graph and task information stored in the database. The workflow manager would iterate through all pending tasks and executes every task not completed and with no dependency on preceding tasks or competing for the microscope hardware.

Each workflow can have multiple distinct phases. Each phase was named by its initial module, the topmost module in the graph. The user would select which phase to execute in the workflow dialog. Providing multiple phases and allowing the user to select between them would give the user the opportunity to split a workflow into sections and perform any required manual adjustments between each phase. For example, in the workflow designs, two phases were exposed; the first performed a low-resolution scan and searched for regions of interest. The second performed a high-resolution tiled imaging of each region of interest found in the first phase.

For tasks tagged as "Serial", child tasks would inherit task configuration from parent tasks. This allowed a form of communication between parent and child tasks in the same workflow phase. For workflows split into separate phases, it may be desirable to pass information from the first phase tasks to the second phase tasks. This cannot be done using task configuration since the second phase tasks were not directly related to the first phase tasks. For these cases, the user can create custom database tables and add identifying information to each record so that the second phase modules can find the associated data. This approach was used in the workflow to pass the position list produced by the region of interest finder in phase 1 of the workflow to the phase 2 imaging module.

Modules were optimized for robustness and rapid processing and acquisition. For modules interfacing with hardware, abstractions and modifications were added to the call sequence to catch aberrant hardware behavior and communication errors. The module would attempt to correct problems or skip the current step before stopping and reporting errors the user. The improvements vastly increased the robustness of the stock µManager software and resulted in requiring user interaction only for hardware problems.

Module API

Figure 11A:
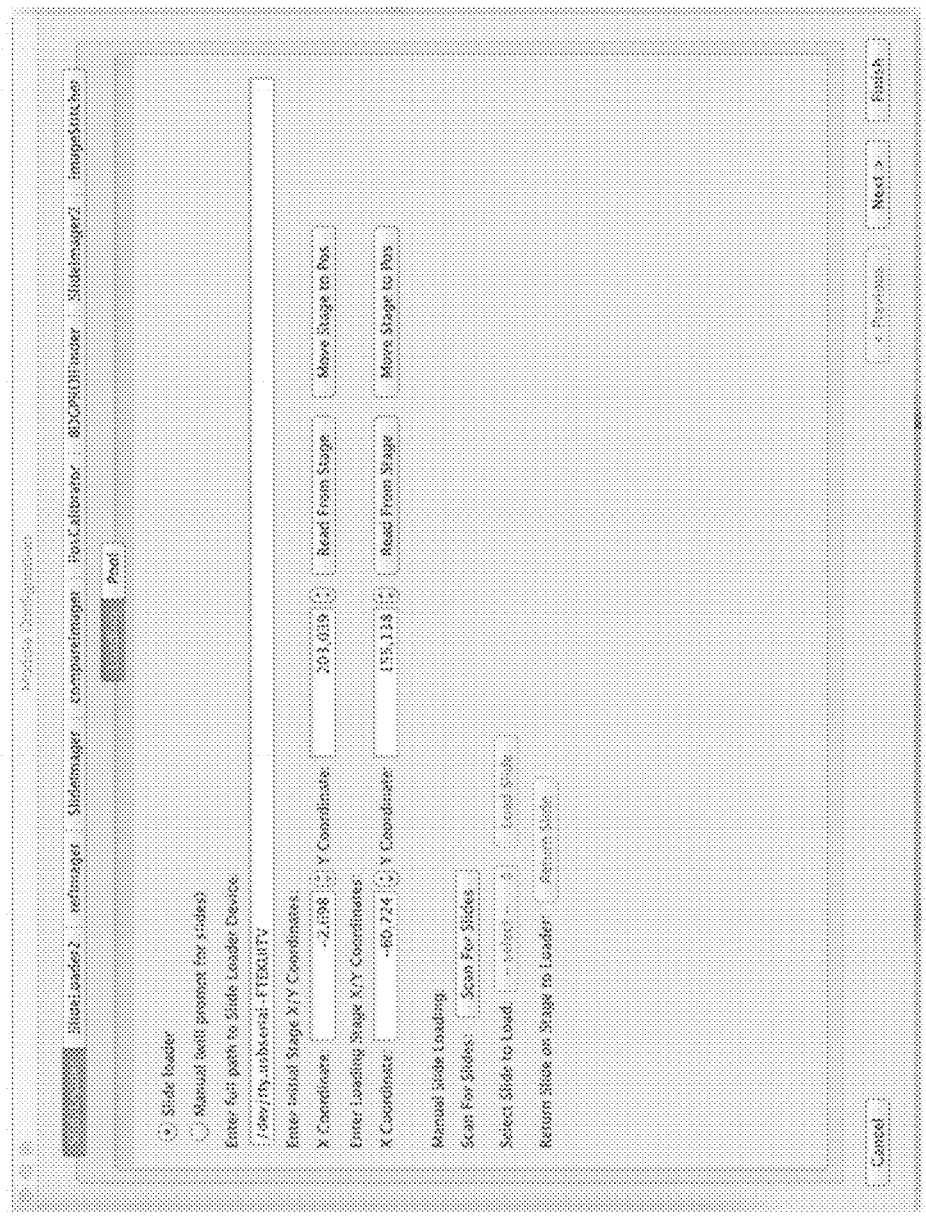
FIGS. 11A-11B show dialogs for module configurations, configurations for the SlideLoader module are shown. Top of the dialog shows a tabbed list for each module in the workflow, remaining part of the dialog shows the currently selected tab.
Figure 11B:
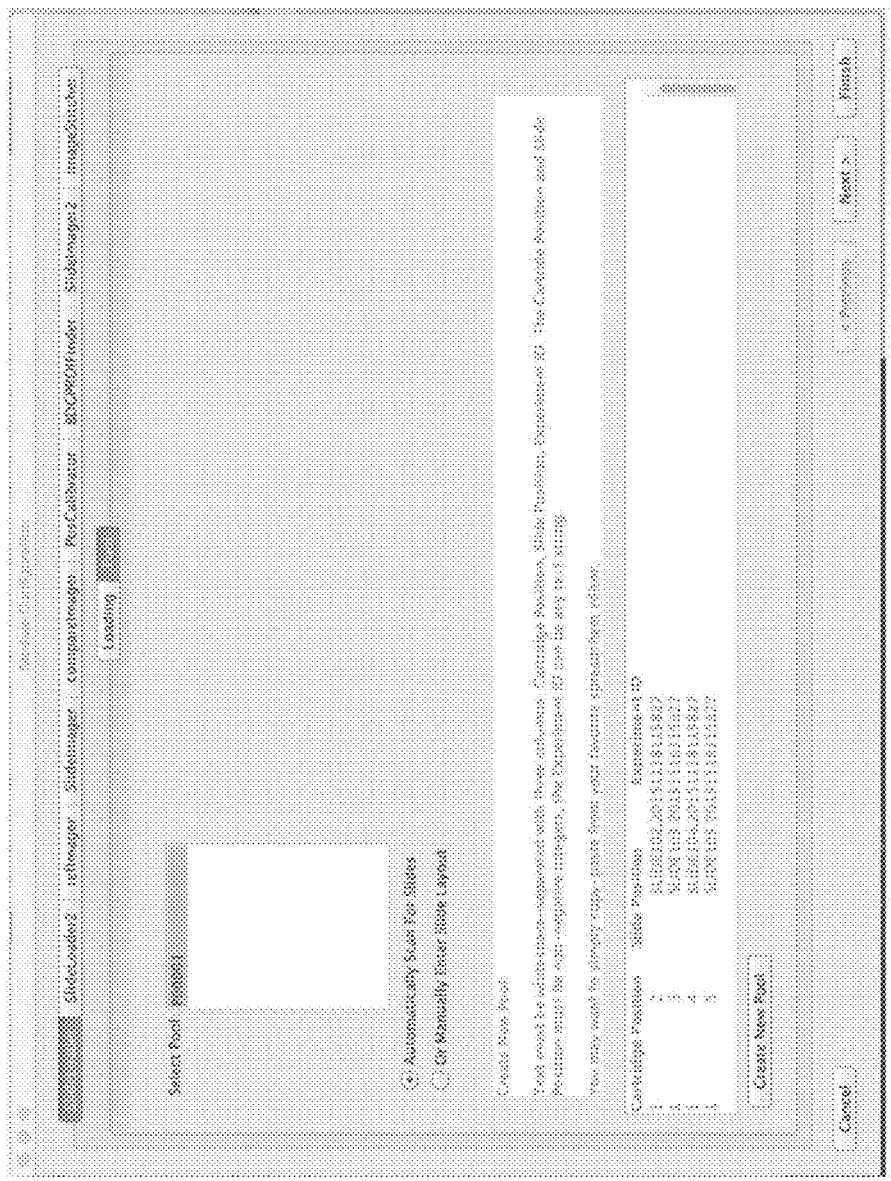

OpenHiCAMM was designed to be easily extensible using modules. Custom modules would need to implement OpenHiCAMM's module interface. The Module interface allowed user-created modules to customize the behavior of their modules using at several key entry points (Table 2). Table 2 shows module API and functions. Custom modules needed to implement the shown functions in order to work as OpenHiCAMM workflow module. Each module can provide a custom configuration user interface (UI). For the configuration UI, a module developer would need to implement a configure( ) method and return a Configuration object. If the module was part of the workflow, the UI would be automatically displayed in the tabbed configuration dialog (FIGS. 11A-11B). The configuration object would be managed and stored in the database by the workflow manager.

TABLE 2

Module API and functions. Custom modules need to implement the shown functions in order to work as OpenHiCAMM workflow module.

| API call | Functionality |
| --- | --- |
| initialize | Called during the workflow initialization phase, before module configuration. Allows the module to perform any required initialization. |
| configure | Called when the user performs the module configuration step. This method returns a Configuration object which handles the configuration UI display, and serialization of configuration options to the database. |

TABLE 2-continued

Module API and functions. Custom modules need to implement the shown functions in order to work as OpenHiCAMM workflow module.

| API call | Functionality |
| --- | --- |
| createTaskRecords | Creates a database record for each task that is expected to be run during the workflow. Called before the start of the workflow run. |
| runInitialize | A second initialization entry point. This point is called before each workflow run, whereas initialize is called only once per module. |
| run | The actual workflow module execution code. Called once per task. |
| cleanup | Task cleanup code. Is called even if the task throws an exception. Called immediately after the run method completes. |
| setTaskStatusOnResume | Allows customization of the task status when the workflow is run in "Resume" mode. |

To add a new module, a module designer can add a Java jar file in the openhicamm_modules directory. On startup, OpenHiCAMM would automatically detect and load all jar files in the openhicamm_modules directory, and the module would be available in the Workflow Design interface. Module designers would be free to design their own database tables, or use the provided configuration object for storing configuration metadata. A thin, easy-to-use wrapper around the popular ORMlite SQL object relational mapping library (http://ormlite.com) was provided in the Connection and Dao classes.

Module Configuration User Interface

The example implementation of OpenHiCAMM illustrated in this example included a module configuration user interface (Table 3). Table 3 shows module configuration user interface API and functions.

TABLE 3

Module configuration user interface API and functions.

| API call | Functionality |
| --- | --- |
| retrieve | Returns the list of configuration key-value pairs retrieved from the configuration UI. |
| display | When given a list of configuration key-value pairs, display returns a Swing Component that contains the configuration UI, with the configuration applied. |
| validate | Scans the configuration UI for any validation errors, and returns a list of ValidationError objects, which is displayed to the user. |

Reporting Interface

OpenHiCAMM included a reporting interface, which a module designer can extend to provide custom workflow reports (Table 4). Table 4 shows report interface API and functions. This reporting interface was used successfully detect and correct implementation bugs and hardware issues in the workflow designs. By clicking the "View Reports" button in the Workflow Dialog, the Report Dialog was displayed with a drop-down list of the reports available for viewing. Module designers can build custom reports by implementing the Report interface and including the report in their plugin JAR file. The report would automatically be detected and added to the list of available reports.

TABLE 4

Report interface API and functions.

| API call | Functionality |
| --- | --- |
| initialize | Pass in the WorkflowRunner context object and perform any required initialization steps. |
| runReport | Run the report and return the contents of the report as an HTML string. |

Reports were created by interfacing with the OpenHiCAMM workflow manager to query the state of the workflow, and producing HTML output for display. To produce HTML with a convenient Java based interface, a HTML templating library named "Tag" was created. The Report UI used the JavaFX WebView component to display the HTML document. JavaScript code can be added to the HTML document. JavaScript was used to interface the report with the microscope hardware, to allow for loading a slide and positioning the stage to a previously imaged object. Once the document was created, it was stored in the workflow directory, and can be re-generated at any time by the user.

Altogether, these data show a workflow implementation and API of OpenHiCAMM.

Example 4

Example Workflow Module Implementation for Detecting Objects of Interest

This example demonstrates a workflow module implementation for detecting objects of interest.

Example Workflow Module Implementation for Detecting Objects of Interest

A ROIFinder module was implemented that executed an image processing pipeline to return an ImageJ ROI list with objects of interest (see the section "ROIFinder and *Drosophila* embryo detection"). The workflow, µManager and Fiji data structures were used to integrate the output of the ROIFinder module in a second phase workflow.

The ROIFinder module created a position list of ROIs and stored it in a custom SlidePosList database table. In the first phase, the SlideImager module processed user defined SlidePosList to determine which areas of the slide will be imaged. In the subsequent phases, the SlideImager module processed the most recently added SlidePosList records. The SlideImager module computed if a region of interest was larger than the size of a single image and created a set of partially overlapping tile positions.

The position list JSON schema defined by µManager allowed for custom properties to be added to each position in the position list. The ROIFinder module added the "stitchGroup" custom property to each position in the ROI tile set to group the individual tiles together. The SlideImager module looked for custom properties in the position list and converted them into task configuration records. Because task configuration was inherited from parent to child for serial tasks, the downstream ImageStitcher module would use the "stitchGroup" task configuration to determine which images need be stitched together.

Core Modules

SlideLoader Module:

The SlideLoader module was responsible for initializing the slide loader hardware, keeping track of which slides were loading and unloading slides to and from the stage. The SlideLoader module defined a high-level programming interface with hardware dependent libraries, similar to the current µManager model. A sample hardware library was developed for a Prior PL-200 slide loader that supported most microscopes and was able to hold and handle up to 200 slides.

SlideImager Module:

The SlideImager module was a wrapper for the µManager Multi-D dialog and acquisition engine, primarily providing configuration storage in the SQL database and invoking the acquisition engine with the previously configured parameters. The position list could be either manually predefined or the result of a previous workflow module, such as the ROIFinder module. To manually create a position list, the µManager position list user-interface was used to define a region on the slide. The SlideImager module would pass configured parameters from the Multi-D dialog and the position list to the Multi-D acquisition engine. All functions provided by the Multi-D dialog were available, able to use all abilities of the µManager, including selectable light filters and stacks along the Z axis. A custom hook to the Multi-D acquisition engine was added, linking back to the SlideImager module, to track the acquisition of each image and schedule post-acquisition image processing tasks.

SlideSurveyor Module

An implementation of the SlideSurveyor module was similar to the SlideImager module in that it can take as its input a position list and acquire images but does not use µManager's Multi-D acquisition module. Instead, the SlideSurveyor module sets the camera to "Live Mode", moving to each position in the list, acquiring a live mode image of the sample. The image was then be copied into an image buffer representing the entire slide. "Live Mode" had the capability of capturing video, which allowed quickly acquiring low-resolution images without triggering the camera's shutter. Running the acquisition in "Live Mode" allowed the SlideSurveyor module to quickly map out an entire slide, even at 20× magnification. The SlideSurveyor module imaged the contents of an entire slide in 20 minutes, as opposed to several hours with the Multi-D module and individual images. The resulting images may be lower quality, but were sufficient for ROI detection.

The same "Live View" mode can also be used to accelerate our custom autofocus engine. The ability to survey an entire slide using the 20× lens avoided using a two-phase workflow, helping the workflow to complete more quickly, and providing more accurate positioning and centering of the ROIs when performing the second phase.

Altogether, these data show that a workflow module implementation of OpenHiCAMM for detecting objects of interest.

Example 5

Calibration of the Slide Position on the Stage

This example demonstrates an example calibration of the slide position on the stage.

Calibration of the Slide Position on the Stage

The PosCalibrator module was developed to processes images from a dedicated instance of the SlideImager module (FIGS. 3A-3D). Both modules can be optionally inserted into the workflow, after the slide is loaded onto the stage. The SlideImager module recorded images at an invariant position and the PosCalibrator module matched the slide position to a previous reference image and adjusted a position list to detected shift.

Figure 3A:
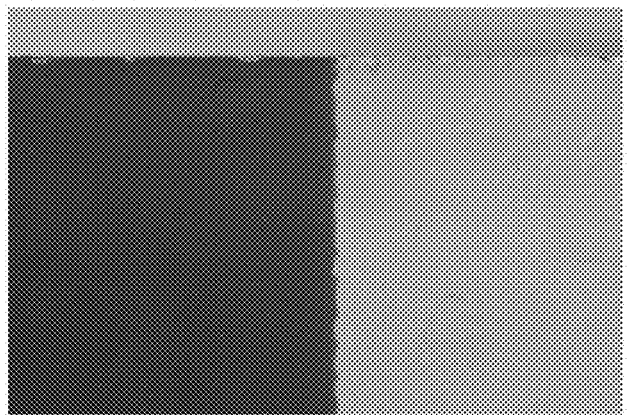
FIGS. 3A-3D show alignment calibration for the same slide, loaded twice and imaged at different magnification.
Figure 3B:
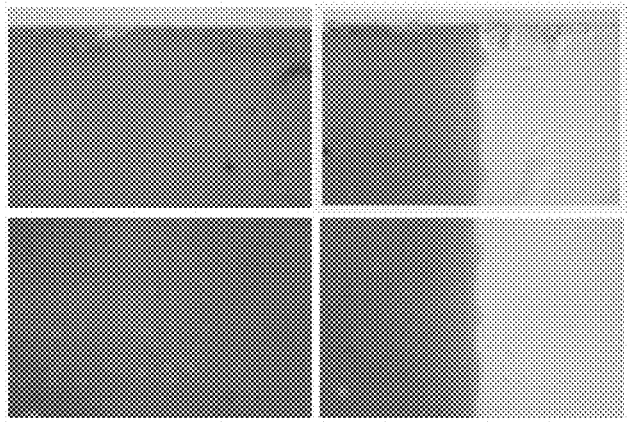
Figure 3C:
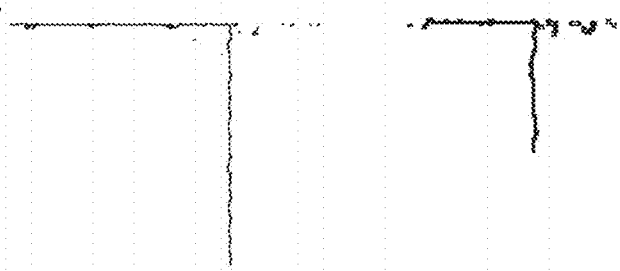

After loading a slide the first time, using the standard SlideImager module (called the refImager module in the example workflow in FIGS. 7A-7B), the user creates a position list with on entry containing the approximate position of a calibration feature. For example, the calibration feature can be the area where the slide frosting and the corner intersect. At each slide, when the workflow reaches the SlideImager module, the user-defined area is imaged and stored as reference (FIG. 3A). At workflows that load the slide again, optionally at different magnifications, the user can create an instance of a modified SlideImager module with additional functionality for re-imaging the area in case of an interrupted workflow (called the compareImager module in FIGS. 7A-7B), followed by the PosCalibrator module. The SlideImager module images the same area again and the images are matched to previously acquired images in the PosCalibrator module, FIG. 3B.

While sophisticated scale and rotation invariant methods have been described, they are generally slow or hard to implement. For the PosCalibrator module, a fast and robust pipeline was created based on Generalized Hough Transform (GHT) template matching. GHT matches the edge contours between a template and a target image by counting matching pixels in an accumulator. For each boundary point of the template, an R-table was pre-computed with the coordinate differences $x_c-x_{ij}$ and $y_c-y_{ij}$ between a fixed reference $x_c/y_c$ in the middle and each boundary point $x_{ij}/y_{ij}$. To account for rotation and scaling scaled and rotated x/y boundary pairs were pre-computed and stored them in the R-table. For each entry in the R-table, the gradient $\Phi(x)$ was calculated. For each pixel in the search image, the pixel gradient was matched to $\Phi$ and a corresponding entry in an accumulator array was increased. The accumulator entry with the maximum value corresponds to the position of the template in the search image.

Figure 3D:
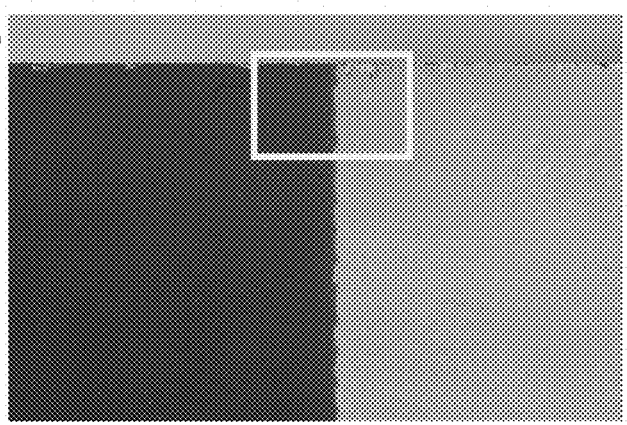

An existing ImageJ plugin, GHT (http://rsb.info.nih.gov/ij/plugins/ght/index.html) was customized. The code in a new plugin was used to encapsulate the pipeline to process and return matched image coordinates as ImageJ ROI. The pipeline converted images to grayscale, resized them and used the ImageJ IsoData algorithm find two thresholding values for the reference and all combined calibration images. The threshold values were used to generate binary images, the images would undergo morphological processing to eliminate holes and errant pixels. From the set of calibration images the pipeline selected an image containing the calibration feature such that both the slide frosting and slide border at roughly or approximately equal proportions. The reference image and the selected calibration image were converted to edge contours (FIG. 3C) for matching with the GHT algorithm (FIG. 3D). The PosCalibrator module would call the plugin and transforms the matched image coordinates to stage coordinates. GHT was scale and rotation invariant but, to further reduce running time, the image sizes was adjusted to the same dimensions with user configurable parameters (e.g. 4 for matching 5× and 20× magnification). Image pixel translations to stage movements were measured with the μManager Pixel Calibration plugin and the resulting values entered as configuration parameters and used to adjust the offset. The modules were tested both with DIC and fluorescent illumination. If no matches are found, a warning message was added to the log and imaging continued with no calibration.

Negligible displacements (FIG. 4) were found with the system. The slide calibration disclosed in this example can work with both light and fluorescent microscope systems.

Altogether, these data show that calibration of the slide position on the stage by OpenHiCAMM.

Example 6

Autofocus

This example demonstrates an example autofocusing.

Autofocus

A plugin, FastFFT, was created using the μManager autofocus API (FIGS. 5A-5C). In FastFFT, the Fast Fourier Transform (FFT) was performed using the Mines Java Toolkit (http://inside.mines.edu/~dhale/jtk/) and a bandpass filter was applied to the power spectrum. The logarithmic values between the two percentage radiuses were summed up and the process repeated for all images in the same stack. The image with the highest value was selected. Empirically, the best bandpass filter between 15 and 80 percent was determined to place the focal point in the middle of the embryo (FIG. 5C). The bandpass filter values can be adjusted in the configuration dialog. To accelerate the image acquisition process, the autofocus module can change the camera setting to live imaging with reduced image size.

FastFFT was compared to two μManager autofocus implementations, J&M and Oughtafocus, by measuring the plugin reported level of detail at multiple stage positions for 10 embryos. The FastFFT module performed as designed and returned highest scoring focal planes at the middle of the embryos (FIGS. 5A, 5C). The μManager functions returned optimal focal planes with more variability, depending on the stage of the embryo (FIG. 5A). At early embryos, focal planes were visually indistinguishable and within 6 μm of each other, less than the thickness of the cell-layer surrounding the blastoderm. At later stages, the μManager functions tended to focus on the surface of the embryo (FIG. 5C). FastFFT performed a magnitude faster than the μManager function (FIG. 5B), an average of 40 seconds for scanning 100 positions, compared to 206 seconds (Oughtafocus) and 246 seconds (J&M). Moreover, FastFFT was more consistent in its speed.

To further speed up processing and cover a wide range of focal planes, a coarse focusing was performed with large interval steps and a broad range and second a finer granularity focusing with small interval steps around the previous best focal plane. Both intervals were user configurable as part of the graphical configuration dialog (for example, taking 41 images at 10 μm intervals and 7 images at 3.3 μm intervals). To prevent hardware damage caused by a potential slow drift in measurements, a configuration was added for an absolute maximum/minimum Z position that cannot be exceeded. The plugin includes a configurable counter to skip focusing on a selected number of images. The counter was reset every time after two consecutive images match the same Z position after completing the autofocus function. This prevented erroneous focusing on occasional mis-detected objects such as air bubbles.

Altogether, these data show implementation and use of the autofocusing feature of OpenHiCAMM.

Example 7

The ROIFinder Module and *Drosophila* Embryo Detection

This example demonstrates ROIFinder and *Drosophila* embryo detection.

ROIFinder and *Drosophila* Embryo Detection

The ROIFinder module processed single images and returned regions of interest (ROI). It provided a high level interface that returns an object's bounding box and can be easily adjusted to custom image processing pipelines. Two computationally efficient ROIFinder module implementations were developed. Two computationally efficient custom ROIFinder module implementations and a macro based implementation, the CustomMacroROIFinder module, were developed. These implementations allowed the user to simply paste a previously developed ImageJ macro into a dialog and execute it as part of the workflow.

The CustomMacroROIFinder module was extremely flexible and along with the powerful Fiji UI and macro recording abilities allowed for the development of complex segmentation workflows by users less experienced with image processing.

One custom implementation can segment the image, use Fiji's "Analyze Particles" function to detect and measure segmented areas and store the bounding boxes for areas exceeding a selectable minimum size. The Analyze Particles function was set to discard objects at the image boundaries. Virtually all objects missed in the *Drosophila* embryo imaging experiment were discarded for crossing image boundaries rather than failure to detect the object.

The simpler the ROIFinder module variant segmented the object by automatic thresholding with IsoData and was suitable for uniform samples distinct from background such as fluorescent labeled samples.

For the work with *Drosophila* embryos, a variant of the ROIFinder module was developed that used the texture, which was frequently inherent in biological samples (e.g., FIG. 5C). The pipeline can call Fiji edge detection, apply a threshold on the edge image with a fixed, empirically determined value (13, out of 255 gray values) and perform morphological image operations (close, fill holes) to smoothen the areas. This pipeline can be suitable for histological samples and other whole mount specimens.

For the SlideSurveyor module, the CustomMacroROIFinder module (FIGS. 6A-6E) was used. The macro was used to 1. remove horizontal and vertical lines that were a result of the SlideSurveyor module's image stitching with Fiji's FFT Bandpass filter plugin, 2. resize, 3. convert to a mask, 4. threshold the image, 5. perform morphological operations and, 6. apply the "Analyze Particles" function as described before.

The ROIFinder module provided a standard API for an image processing pipeline and using Fiji's image processing plugins, programming and macro recording abilities, a customized pipeline can be easily implemented. More complex samples such as mutant embryos with altered developmental phenotypes can be detected and rapidly imaged at high resolution for computational analysis. Sample specific object detection pipelines can be implemented, which can significantly increase the throughput if uninteresting objects can be discarded at low resolution.

Altogether, these data show using the ROIFinder module of the OpenHiCAMM software for *Drosophila* embryo detection.

Example 8

*Drosophila* Embryo Imaging Workflow

Figure 8:
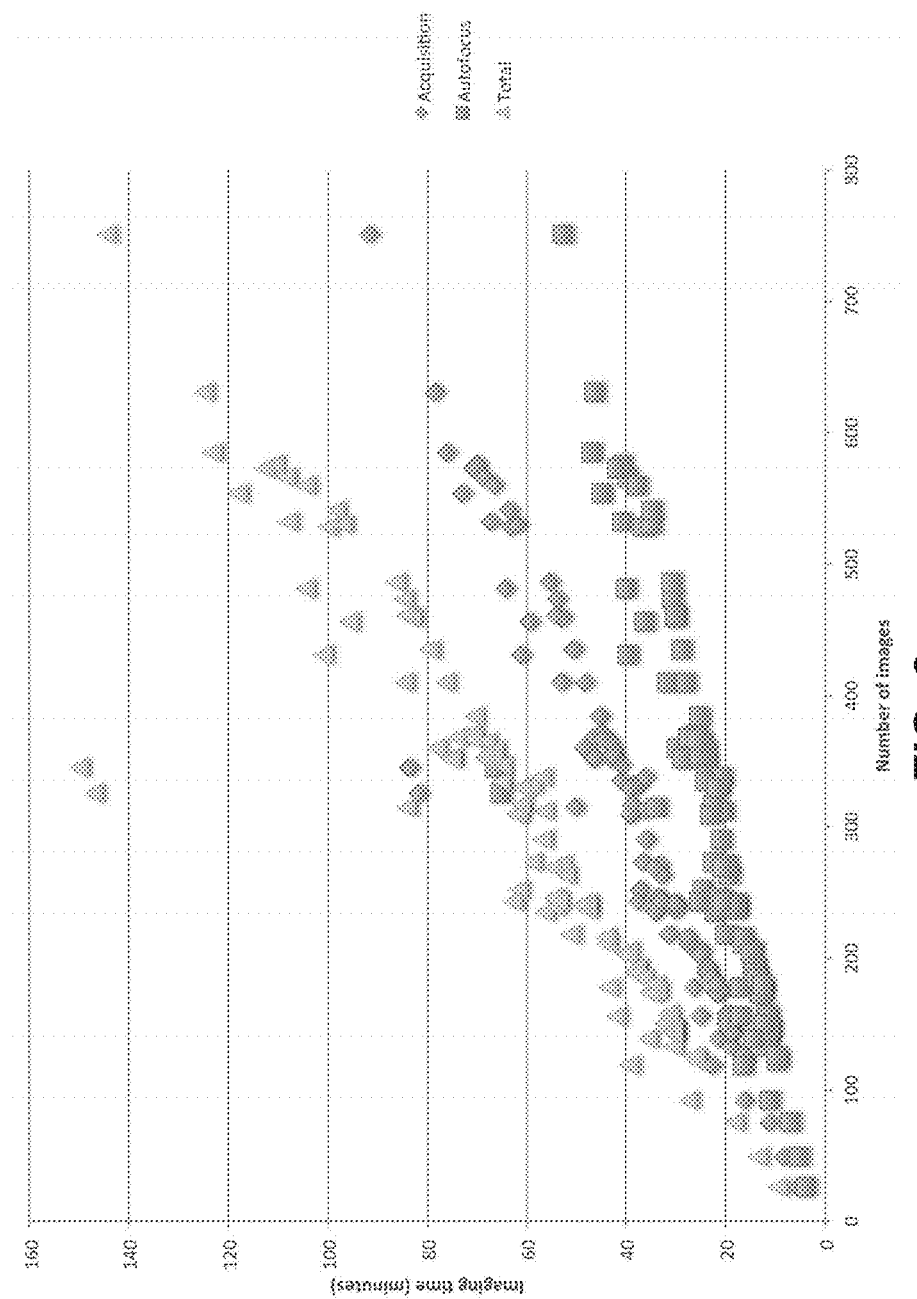
FIG. 8 shows times for imaging 95 slides from a 96-well experiment with *Drosophila* embryo samples. The time in minutes is shown on the vertical axis, the number of images on the horizontal axis. The 90% percentile, i.e. 5% to 95%, is between 119 and 573 images. Acquisition times vary according to the success of the autofocus process.
Figure 10A:
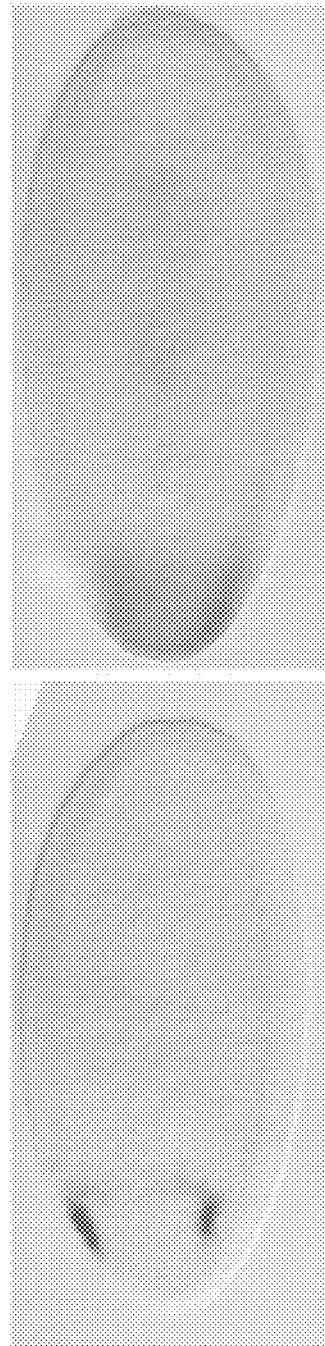
FIGS. 10A-10B show additional supporting images for the mirror (mir) CRM experiment.
Figure 10B:
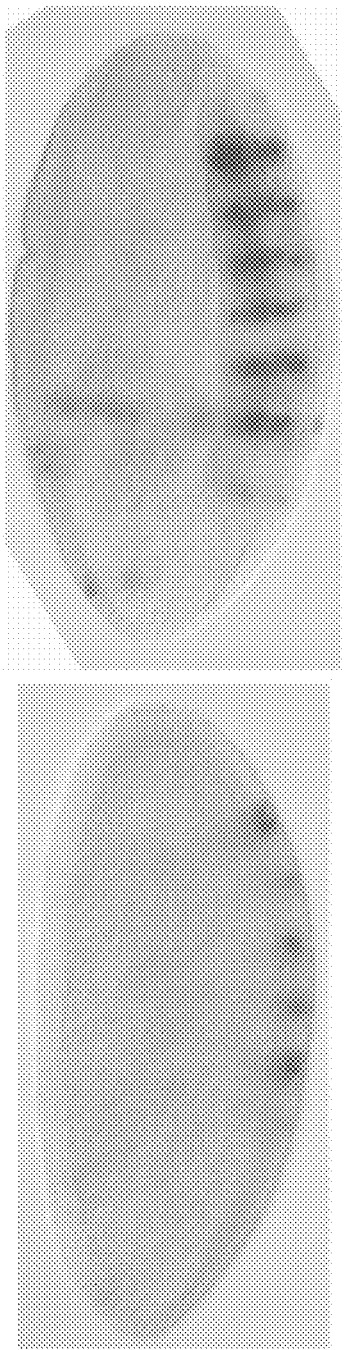

This example demonstrates *Drosophila* embryo imaging.
*Drosophila* Embryo Imaging Workflow
The two phase workflow (FIGS. 7A-7B) was used. After loading the slides, the SlideImager module captured images with a given list of positions on the slide. The initial position list was configured by the user as the maximum area of interest and slides are imaged in overlapping tiles at 5× magnification. Captured images were processed with a module, the ROIFinder module, to detect objects and their coordinates stored in the database. Detected objects were stored as bounding boxes, transformed to the imaging area and the content of the bounding boxes imaged again at higher resolution (FIGS. 8 and 10A-10B). If a bounding box exceeded the size of a single image at 20×, multiple tiled images were acquired and post-processed with a module, the ImageStitcher module, using an Fiji stitching algorithm to assemble a composite image (FIGS. 2D and 10A-10B).

The Fiji based stitching worked reliably for 2-3 images but failed frequently for large composites with 3 or more images. These large composites contained dense clusters of overlapping embryos and discarded the results.

Figures 9A, 9B:
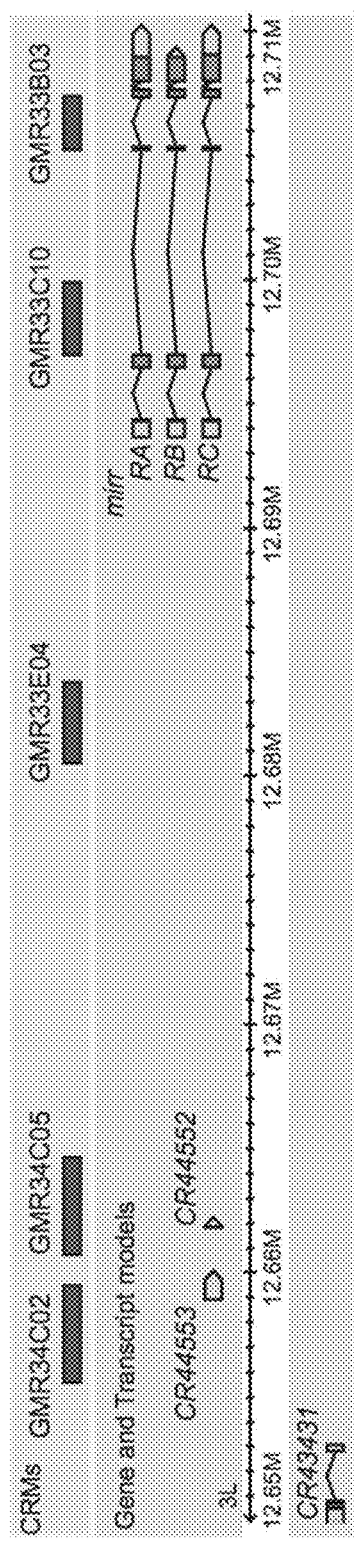
FIGS. 9A-9B show images acquired with OpenHiCAMM for wild-type in situ hybridizations with a probe against the gene mirr and CRM constructs with probes against Gal4.
Figure 13:
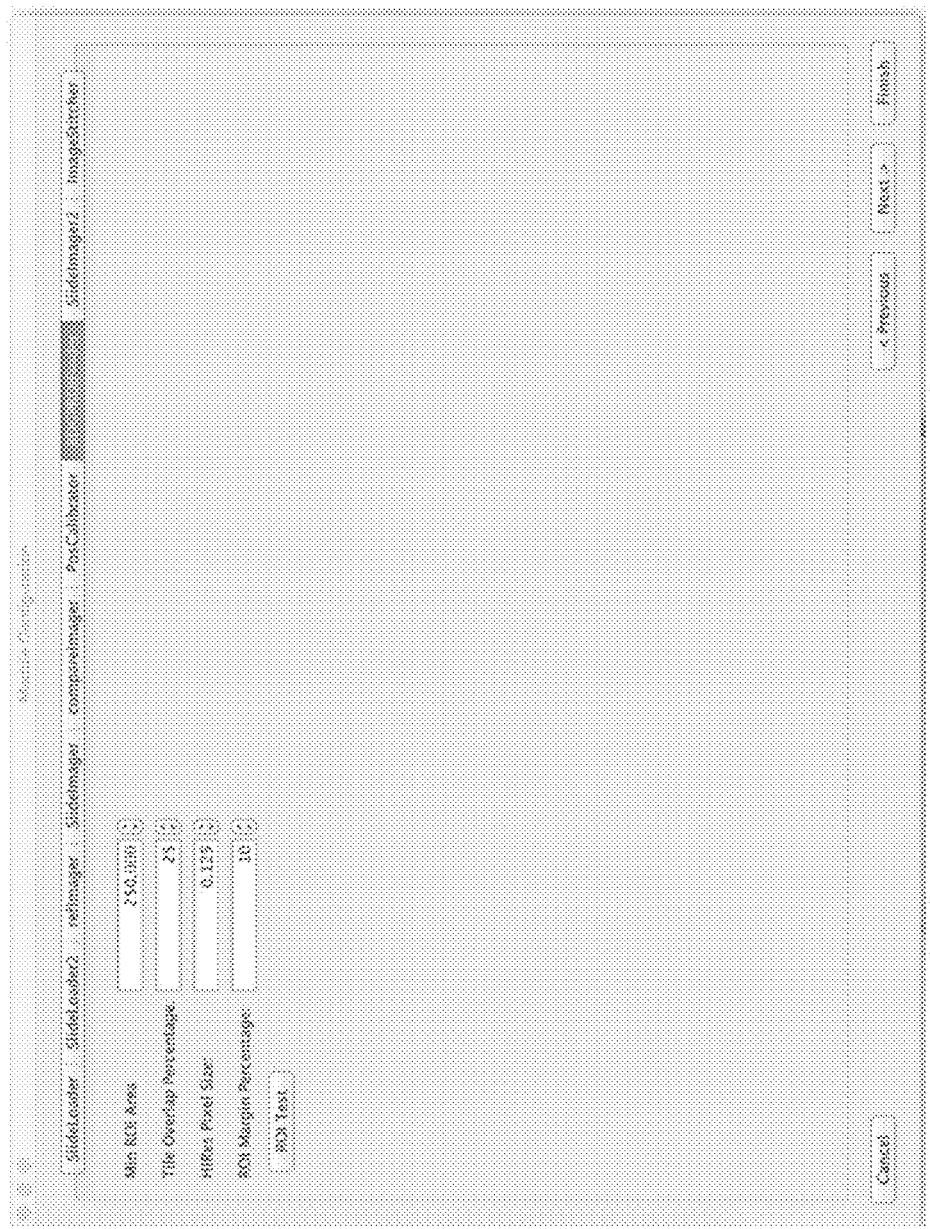
FIG. 13 shows a dialog for module configurations, shown is a ROIFinder module. The implementation of the ROIFinder module required a configuration for a minimum size of an object to be recorded (top line), the overlap to adjacent images, the pixel size (FIGS. 11A-11B) and a configurable increase for the detected bounding box size.
Figure 14A:
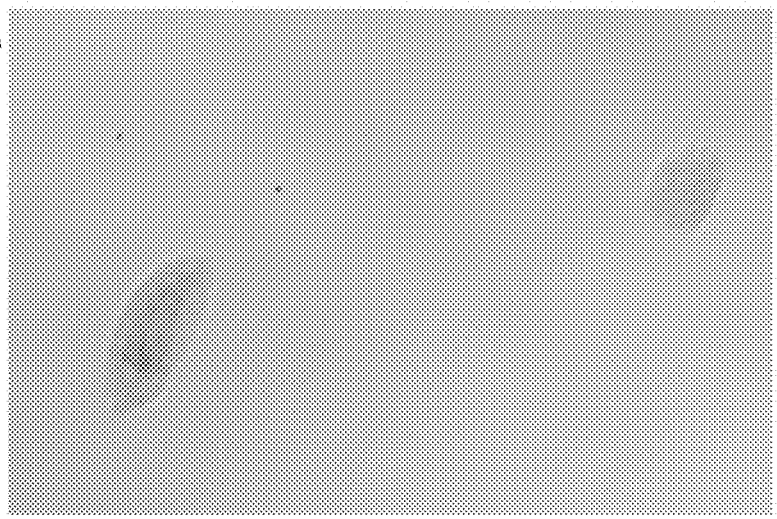
FIGS. 14A-14C show generic objects found by the ROIfinder module.
Figure 14B:
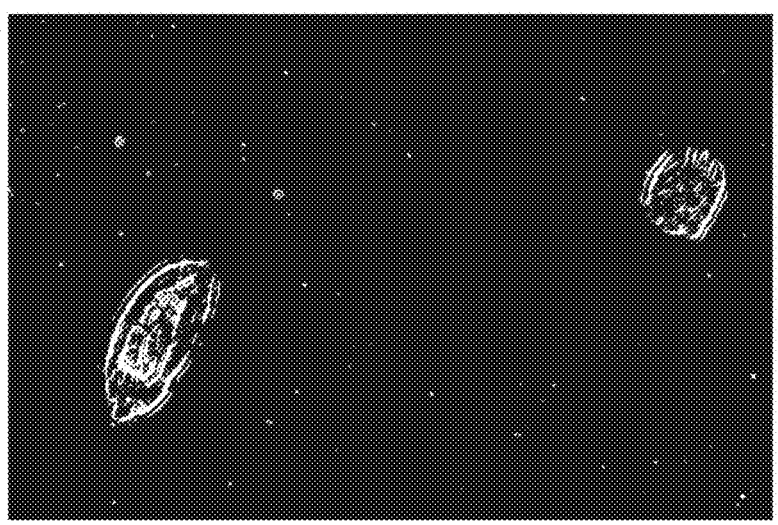
Figure 14C:
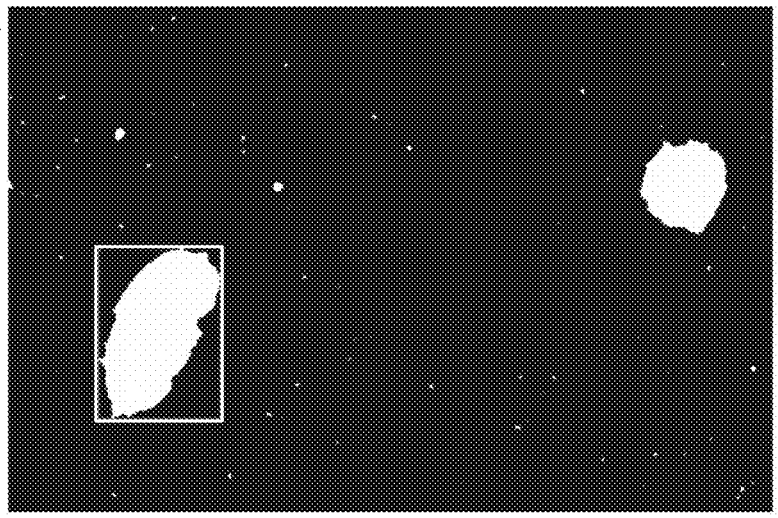

Six slides were imaged to compare *Drosophila* embryonic wild type gene expression of the gene mirror (mirr) with two intragenic and three intergenic cis-regulatory module (CRM) reporter constructs (FIGS. 9A-9B and 13). For good quality slides, the workflow acquired over 75-85% of the objects on the slide. One slide (GMR33E04) exhibited age related degradation (low contrast) and detected only 55% of the total objects on the slide. For each slide, high quality images were obtained, and a set of standard orientations was recovered to compare and evaluate expression patterns (FIGS. 9A-9B). The five CRMs produced a subset of the wild type gene expression pattern, except for GMR33C10 at stage range 4-6 which showed a segmental pattern not seen in the mir wild type. The GMR33C10 segmental continued to stage range 7-8 (FIG. 10B) and then became restricted to a subset of the wild type pattern at stage range 9-10, suggesting that this CRM lacks a critical repressive DNA component of the enhancer element. Altogether, these data show *Drosophila* embryo imaging using the SlidImager, ROIFinder, and ImageStitcher modules of the OpenHiCAMM software.

Example 9

User Interface

This example demonstrates a user interface of OpenHiCAMM.
User Interface
The main window was available from the µManager plugin menu (FIGS. 2A-2D). The user can select a local or remotely mounted (NFS or CIFS) directory as location for the workflow database, settings and images.

Using a workflow editor, the user can add and arrange modules from an existing set to create a workflow (FIGS. 7A-7B). For one low/high magnification implementation, a combined workflow was created with two imaging phases. The first imaging phase included the SlideLoader module, the refImager module, the SlideImager module and the ROIFinder module, the second imaging phase include the compareImager module, the PosCalibrator module, another instance of the SlideImager module and the ImageStitcher module. Modules for the second imaging phase can automatically detect and use results from the first imaging phase. When the workflow reached a point with no child tasks, it will terminate.

The "Start Task" in the main window can define the entry point, in the implementation, either the first or second imaging phase.

Figure 12:
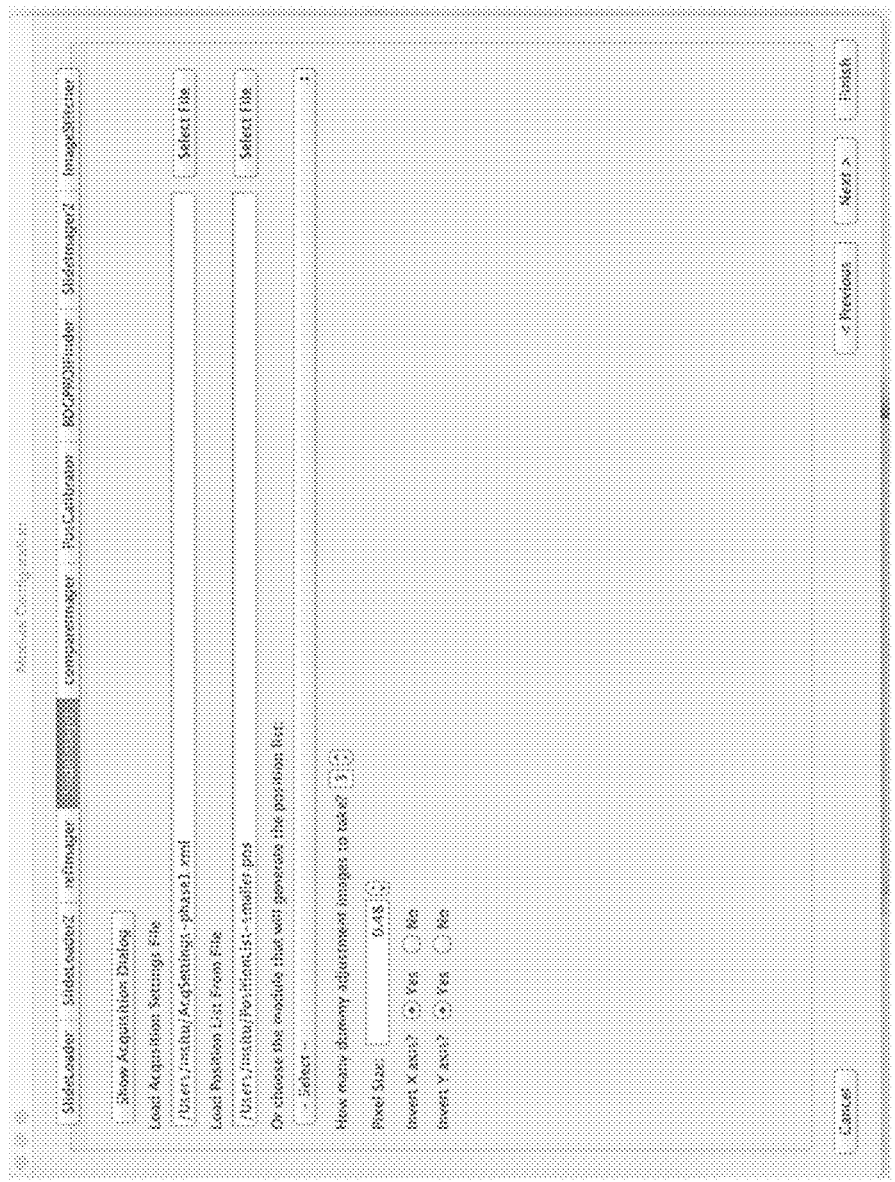
FIG. 12 shows a dialog for module configurations, shown is the SlideImager module. Settings can be configured and saved with the µManager Multi-D dialog (button "Show acquisition dialog"), settings from the Multi-D dialog can be assigned, and a user defined position list or a previously computed position list selected. Some cameras were found to need more time to adjust to the light. Thus a configuration option was added to take a selectable number of "dummy" images before starting the imaging. The pixel size needed to be calibrated with µManager and entered as configuration to adjust the pixels in the images to the stage position. Additional options were added to invert the coordinates for the stage compared to the captured image, if necessary.

Each workflow module can be configured with persistent settings in a configuration dialog called from the main window (FIGS. 11A-11B and 12-13). The SlideLoader module created a pool of slides with the current slides in the robotic slide loader, allowed for scanning the slides and adding meta-data information (FIGS. 11A-11B). The SlideImager module called the μManager Multi-D dialog for configuration of the slide imaging task and saved the settings in the workflow database (FIG. 12). The SlideImager module's derived modules, the refImager and compareImager modules, were configured similarly. The refImager module takes a reference image for calibration at a user defined position. The compareImager module captured an overlapping set of images centered around the user defined position of the refImager module. Upon successful completion, the image captured by the refImager module and the set of images captured by the compareImager module were used by the PosCalibrator module to identify the matching position (see Detection of the slide position) and adjusted the position coordinates. The ROIFinder module can be configured to record objects of a user defined minimum size and tested on images in the configuration dialog (FIG. 13). Testing the ROI finder opened a window with images for each intermediate processing step and the resulting bounding boxes as illustrated in FIGS. 6A-6E and 14A-14C.

For each defined workflow, new instances were used for processing a pool of slides. Thus, the same basic configuration can be used for multiple slide pools. Image files were stored in μManager format in a folder set by the initial workflow configuration and sub-folders matching the workflow instance and workflow tasks, respectively.

The workflow progress was stored in a SQL database. For debugging or correcting unexpected problems, the Workflow Dialog included a "Show Database Manager" button that opened a graphical database-querying interface with the workflow database loaded. The OpenHiCAMM source also included a "sqltool" command-line script which, when run in the workflow directory, opened a command-line SQL query tool, which was useful for debugging purposes.

Altogether, these data show using an example user interface of OpenHiCAMM.

Example 10

Reviewing Results

This example demonstrates reviewing the results using OpenHiCAMM.

Reviewing the Results

Figure 15:
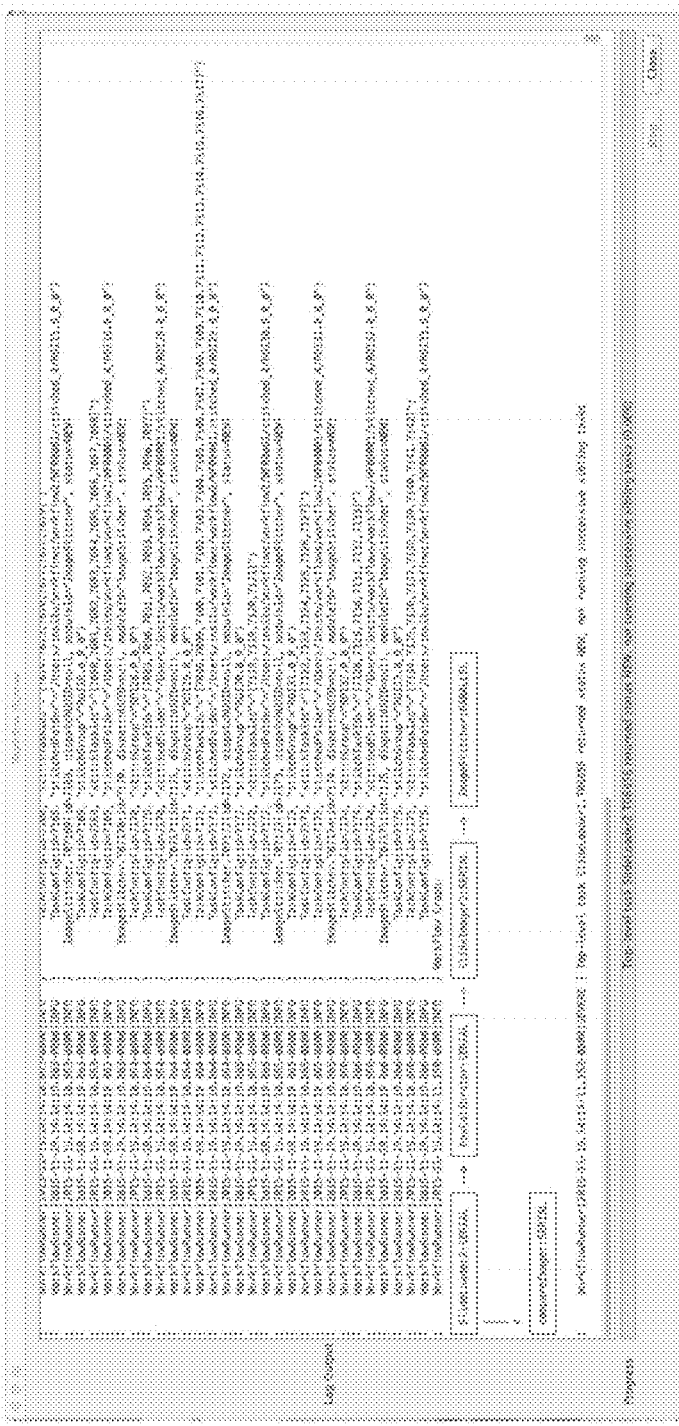
FIG. 15 shows a log output during running the workflow. Initially the workflow manager computed all tasks to complete the currently configured workflow and adds them to the persistent database. The workflow manager displayed the currently configured workflow and the tasks that need to be completed sequentially because of hardware dependencies ("SERIAL") or can be executed in parallel ("PARALLEL"), only those modules dependent on computations in one embodiment. Progress for each task was printed as log messages, and the overall progress and remaining time shown in a progress bar (bottom).

During workflow processing, progress can be monitored with a live imaging view and a log window (FIG. 15). Workflows can be stopped and resumed at defined checkpoints. Upon completion, results can be visualized in an HTML report.

Figure 16:
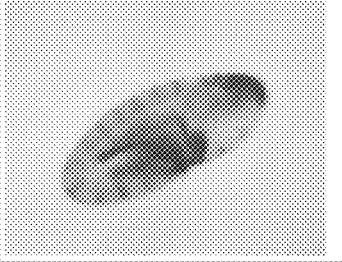
FIG. 16 shows a summary report after acquisition. Shown is a screenshot from the browser. Hyperlinks on the left allow for loading the slide and positioning at the location of the object. The images on the left are from low resolution (5×) phase 1, middle are composite of roughly tiled (according to coordinate position) high resolution phase 2 images (20×), and right composite images showing the result of the image stitching module.

At the conclusion of the pipeline, OpenHiCAMM generated a summary report, displaying the calibration images, and the results for all imaging passes. The report was generated as an html file (FIG. 16) and rendered in OpenHiCAMM in a report window. In OpenHiCAMM, the report viewer allowed for loading slides and positioning the stage to positions. The report file can also be independently opened and viewed in a standard web browser.

Altogether, these data show using OpenHiCAMM to monitor progress with a live imaging view and a log window and display results of all imaging passes.

Example 11

In Situ Hybridization

This example demonstrates in situ hybridization experiments.

In Situ Hybridization Experiments

In situ hybridizations were performed as previously described (Weiszmann et al., Determination of gene expression patterns using high-throughput RNA in situ hybridization to whole-mount *Drosophila* embryos, Nat. Protoc. 2009, 4(5):605-18; the content of which is incorporated herein by reference in its entirety). In brief, an RNA probe made from a cDNA clone of mirror was used to hybridize fixed wild type embryos, and a probe that detects Gal4 reporter RNA was used to hybridize fixed embryos of five engineered *Drosophila* strains, GMR33C02, GMR33C05, GMR33E04, GMR33C10, GMR33B03, from the Janelia Farm Research Campus (JFRC) FlyLight Gal4 collection, each carrying a putative mirror enhancer with a Gal4 reporter.

Embryos were mounted on slides and imaged with OpenHiCAMM.

Altogether, these data show experimental conditions of in situ hybridization.

It is to be understood that not necessarily all objects or advantages may be achieved in accordance with any particular embodiment described herein. Thus, for example, those skilled in the art will recognize that certain embodiments may be configured to operate in a manner that achieves or optimizes one advantage or group of advantages as taught herein without necessarily achieving other objects or advantages as may be taught or suggested herein.

All of the processes described herein may be embodied in, and fully automated via, software code modules executed by a computing system that includes one or more computers or processors. The code modules may be stored in any type of non-transitory computer-readable medium or other computer storage device. Some or all the methods may be embodied in specialized computer hardware.

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks and modules described in connection with the embodiments disclosed herein can be implemented or performed by a machine, such as a processing unit or processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

Conditional language such as, among others, "can," "could," "might" or "may," unless specifically stated otherwise, are otherwise understood within the context as used in general to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Further, the term "each", as used herein, in addition to having its ordinary meaning, can mean any subset of a set of elements to which the term "each" is applied.

Any process descriptions, elements or blocks in the flow diagrams described herein and/or depicted in the attached figures should be understood as potentially representing modules, segments, or portions of code which include one or more executable instructions for implementing specific logical functions or elements in the process. Alternate implementations are included within the scope of the embodiments described herein in which elements or functions may be deleted, executed out of order from that shown, or discussed, including substantially concurrently or in reverse order, depending on the functionality involved as would be understood by those skilled in the art.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for high content screening and microscope imaging of a sample, comprising:
   obtaining a reference image of a calibration feature from a slide mounted on a microscope;
   obtaining a plurality of first modality images of the slide based on a first modality;
   determining a plurality of regions of interest at a plurality of image positions in the plurality of first modality images of the slide;
   obtaining a comparison image of the slide around the calibration feature;
   determining an offset between an image position of the calibration feature in the reference image and an image position of the calibration feature in the comparison image;
   updating the plurality of image positions based on the offset; and
   obtaining a plurality of second modality images of a plurality of regions of interest at the plurality of updated image positions based on a second modality.

2. The method of claim 1, wherein sample comprises *Drosophila* embryos.

3. The method of claim 1, wherein the plurality of first modality images comprises a plurality tiled images.

4. The method of claim 1, wherein the calibration feature comprises an intersection between frosting of the slide and a corner of the slide, and wherein the frosting of the slide and the corner of the slide in the comparison image have approximately equal proportions.

5. The method of claim 1, wherein the plurality of regions of interest at the plurality of image positions comprises a plurality of boxes at the plurality of image positions.

6. The method of claim 1, wherein determining the plurality of regions of interest comprises determining the plurality of regions of interest at the plurality of image positions in the plurality of images of the slide based on sample texture.

7. The method of claim 1, wherein obtaining the comparison image comprises obtaining a plurality of comparison images of the slide around the calibration feature, and wherein the plurality of comparison images comprises the comparison image.

8. The method of claim 1, wherein the method further comprises receiving an approximate position of the calibration feature on the slide.

9. The method of claim 1, wherein determining the offset comprises determining, using Generalized Hough Transform, the offset between an image position of the calibration feature in the reference image and an image position of the calibration feature in the comparison image.

10. The method of claim 1, wherein the offset is in an image coordinate system, and wherein determining the offset comprises determining an offset in a stage coordinate system based on the offset in the image coordinate system.

11. A system for high content screening and microscope imaging, comprising:
    a microscope comprising a motorized stage, a camera and a robotic slide loader;
    a reference imager module for capturing, using the camera, a reference image of the slide on the motorized stage at a first stage position;
    a slide imager module for capturing, using the camera, a plurality of first modality, tiled images based on a first modality and a plurality of second modality images at a plurality of regions of interest based on a second modality;
    a region of interest finder module for determining the plurality of regions of interest at a plurality of image positions in the plurality of first modality, tiled images;
    a compare imager module for capturing, using the camera, a plurality of tiled comparison images around the first stage position; and
    a position calibrator module for determining an offset between the reference image and the plurality of tiled comparison images.

12. The system of claim 11, wherein the system further comprises user interface for receiving the stage position from a user.

13. The system of claim 11, wherein the plurality of modules further comprises a slide surveyor for capturing, using a live view mode of the camera, a plurality of low resolution images of the slide.

14. The system of claim 11, wherein tasks of each of the pluralities of tasks are linked as an acyclic graph.

15. The system of claim 11, wherein tasks of the pluralities of tasks comprise serial and parallel tasks.

16. The system of claim 11, further comprising an image stitcher module for stitching two second modality images of the plurality of second modality images to generate an image of a region of interest based on the second modality.

17. The system of claim 11, wherein the first modality comprises a lower magnification level, and wherein the second modality comprises a higher magnification level.

18. The system of claim 11, wherein the first modality comprises a live view mode, and wherein the second modality comprises a shutter mode.

19. The system of claim 11, wherein the first modality comprises a first microscope, and wherein the second modality comprises a second microscope.

20. The system of claim 11, wherein the first modality comprises a first illumination condition, and wherein the second modality comprises a second illumination condition.

21. The system of claim 11, further comprising a slide loader module for unloading the slide from the motorized stage, using the robotic slide loader, after capturing the plurality of first modality, tiled images, and reloading the slide onto the motorized stage, using the robotic slide loader, prior to obtaining the plurality of tiled comparison images.

22. The system of claim 11, wherein the slide imager module is configured to focus on a region of interest at an updated image position prior to capturing a second modality image of the region of interest at the updated image position.

23. The system of claim 22, wherein the region of interest is focused using Fast Fourier Transform.

* * * * *